US012172334B2

(12) United States Patent
Lomeli et al.

(10) Patent No.: US 12,172,334 B2
(45) Date of Patent: Dec. 24, 2024

(54) ACCESS PORT CUTTERS AND RELATED METHODS

(71) Applicant: Medos International Sarl, Le Locle (CH)

(72) Inventors: Roman Lomeli, Plymouth, MA (US); Jae Stelzer, Norton, MA (US); Nicholas Pavento, North Attleboro, MA (US); Alicia McDermott, Waltham, MA (US); Paul Maguire, Hope Valley, RI (US); Christopher Ramsay, West Wareham, MA (US)

(73) Assignee: Medos International Sárl, Le Locle (CH)

( * ) Notice: Subject to any disclaimer, the term of this patent is extended or adjusted under 35 U.S.C. 154(b) by 1064 days.

(21) Appl. No.: 16/917,777

(22) Filed: Jun. 30, 2020

(65) Prior Publication Data

US 2021/0401450 A1    Dec. 30, 2021

(51) Int. Cl.
  *B26D 3/16* (2006.01)
  *A61B 17/3211* (2006.01)
  (Continued)

(52) U.S. Cl.
  CPC .......... *B26D 3/169* (2013.01); *A61B 17/3211* (2013.01); *A61B 17/3421* (2013.01);
  (Continued)

(58) Field of Classification Search
  CPC .. B26D 3/169; B23D 21/06; A61B 2017/3443
  See application file for complete search history.

(56) References Cited

U.S. PATENT DOCUMENTS

| 5,218,765 A | 6/1993 | Huang | |
| 5,862,593 A * | 1/1999 | Huang | B26D 3/169 |
| | | | 30/92 |

(Continued)

FOREIGN PATENT DOCUMENTS

| CN | 104786244 A | * | 7/2015 |
| CN | 204604374 U | | 9/2015 |
| CN | 106903739 B | | 7/2018 |

OTHER PUBLICATIONS

International Search Report and Written Opinion Application No. PCT/EP2021/067961, dated Jun. 10, 2021 (12 pages).

(Continued)

*Primary Examiner* — Jennifer S Matthews
(74) *Attorney, Agent, or Firm* — Barnes & Thornburg LLP

(57) ABSTRACT

Access port cutters and related systems and methods can be used to cut an access port to a desired length based on particular patient and/or surgical procedure needs at a point of use. More particularly, an access port cutter can include a base with an opening that can receive an access port therein such that a desired length of the access port can extend from the opening. An actuation mechanism can translate a blade linearly along at least a portion of the base such that the blade can traverse the opening and cut across the access port. In some embodiments, the actuation mechanism can include a handle that can pivot relative to the base to drive the blade. One or more safety features can reduce the risk of inadvertent actuation of the blade and/or prevent debris from contaminating a surgical site or falling onto a patient.

17 Claims, 27 Drawing Sheets

(51) Int. Cl.
*A61B 17/34* (2006.01)
*B26D 1/08* (2006.01)
*B26D 7/02* (2006.01)

(52) U.S. Cl.
CPC ...... *A61B 17/3423* (2013.01); *A61B 17/3494* (2013.01); *A61B 2017/3443* (2013.01); *B26D 1/08* (2013.01); *B26D 7/02* (2013.01)

(56) References Cited

U.S. PATENT DOCUMENTS

| | | |
|---|---|---|
| 6,085,425 A | 7/2000 | Weber |
| 6,159,179 A | 12/2000 | Simonson |
| 8,968,420 B2 | 3/2015 | Beale et al. |
| 9,108,324 B1 | 8/2015 | Chandrasekar et al. |
| 10,525,607 B1* | 1/2020 | Vayntraub ................ B25G 1/10 |
| 2006/0052818 A1 | 3/2006 | Drake et al. |
| 2008/0189954 A1* | 8/2008 | Lin ........................ B23D 21/10 |
| | | 30/92 |
| 2009/0158597 A1 | 6/2009 | Braga et al. |
| 2011/0106125 A1 | 5/2011 | Steele et al. |
| 2011/0144447 A1* | 6/2011 | Schleitweiler ..... A61B 17/3421 |
| | | 600/210 |
| 2013/0035542 A1 | 2/2013 | Morningstar et al. |
| 2013/0035543 A1 | 2/2013 | Fischer et al. |
| 2013/0213202 A1 | 8/2013 | Crainich |
| 2018/0021059 A1 | 1/2018 | Dolgin et al. |

OTHER PUBLICATIONS

International Preliminary Report on Patentability for Application No. PCT/EP2021/067961, dated issued Dec. 13, 2022 (7 pages).

* cited by examiner

ACCESS PORT CUTTERS AND RELATED METHODS

FIELD

Access port cutters and related methods are disclosed herein, e.g., for cutting an access port to a customizable length suitable for a particular patient and/or surgical procedure at the point of use, e.g., in an operating room and/or surgical field.

BACKGROUND

In a surgical procedure, an access port can be inserted through an incision in a patient to provide access to and visualization of a surgical site. A distance of access to a surgical site and, accordingly, a length of an access port required for accessing the surgical site, can depend on one or more factors that may vary based on a particular patient and/or procedure. For example, location of a surgical procedure, access approach to the surgical site, and/or patient particularities, such as age, body mass index, height, condition of particular anatomy, etc., can impact a required length of the access port.

One known solution for such varying dimensional requirements can be to use a standard access port for every procedure with a length long enough to ensure that it will reach from a surface of a patient's skin to a surgical site in most, if not all patients. Long ports, however, can have several drawbacks that can make using a port that extends well beyond a needed length a sub-optimal solution. For example, longer ports require longer instruments which can reduce accuracy and control of the instrument by a user. Longer ports can also reduce the angles of instrument approach, effective operating area, and visibility of the operating area by a surgeon. Moreover, longer ports can increase a distance from the surgeon to the operating area which can increase eye fatigue and/or physical strain on the surgeon.

Another known solution can be to provide a vast number of fixed length access ports of varying lengths in the operating room or operating area such that a surgeon can select a particular access port with an optimal length during the procedure. This, however, can require a large number of access ports to be prepared for a procedure in which only a single access port is used. The unused ports can decrease operational efficiency, e.g., require time to prepare unused ports, take up space in the operating room, require reprocessing following the procedure, etc. Another possible approach can be to customize a length of an access port during the surgical procedure using a cutting device. Known cutting devices, however, suffer from drawbacks such as injury to a user from a cutting surface, injury to a user from poor ergonomics of the cutting device, deformation of the access port during and following a cut, and/or debris ejected from the access port during cutting impacting or contaminating the patient and/or surgical site.

Accordingly, there is a need for improved systems, methods, and devices for cutting an access port to a desired length at a point of use, e.g., in a surgical field, with reduced risk of injury to a user and patient, and reduced risk of contamination of a surgical site without negatively impacting operational efficiency or complicating the surgical procedure.

SUMMARY

Access port cutters and related methods are disclosed herein for tailoring a length of an access port to needs of a particular patient and/or surgical procedure at a point of use, e.g., in an operating room, surgical field, etc., in a safe manner while maintaining integrity of the access port. The access port cutter can include a base with an opening that can receive an access port therein such that a desired length of the access port can extend from the opening. An actuation mechanism can translate a blade linearly along at least a portion of the base such that the blade can traverse the opening and cut across the access port. In some embodiments, the actuation mechanism can include a handle that can pivot relative to the base to drive the blade. One or more safety features can reduce the risk of inadvertent actuation of the blade and/or prevent debris from contaminating a surgical site or falling onto a patient. In some embodiments, the access port cutter can be configured for use by a surgeon over a patient or at a surgical site, while in other embodiments, the access port cutter can be used on a back table away from the patient.

In one aspect, an access port cutter can include a base with an opening that can receive a surgical access port therein, a blade that can translate linearly along at least a portion of the base, and an actuation mechanism. The actuation mechanism can linearly translate the blade along at least a portion of the base such that the blade traverses the opening to cut through a surgical access port received within the opening.

The devices and methods described herein can have a number of additional features and/or variations, all of which are within the scope of the present disclosure. In some embodiments, for example, the linear actuation mechanism can further include a handle pivotably connected to the base. Pivoting the handle relative to the base can linearly translate the blade. In some such embodiments, the handle can include a first engagement feature and the blade can include a second engagement feature. The first engagement feature can be configured to engage with the second engagement feature to linearly translate the blade along the at a portion of the base. The first engagement feature can be a pinion gear and the second engagement feature can be a gear rack. In some embodiments, the blade can be part of a blade cartridge that can be slidably received within the base portion. The blade cartridge can include a retention feature configured to hold the blade away from the opening.

The access port cutter can further include a lock feature to prevent operation of the actuation mechanism. In some embodiments, the lock feature can be a bi-directional lockout pin that can extend through the actuation mechanism. In some embodiments, the instrument can include an extension that can circumscribe the opening and can extend proximally therefrom. In some such embodiments, the extension can include at least one interference feature that can engage waste material of an access port body received within the opening.

In another aspect, a surgical system can include an access port having a proximal end, a distal end, and a lumen extending therebetween and an access port cutter. The access port cutter can have at least one opening to receive the access port therein, a blade, and an actuation mechanism. The actuation mechanism can be configured to linearly translate the blade to cut across the access port received within the opening.

In some embodiments, the at least one opening of the access port cutter can include a plurality of openings. A first opening of the plurality of openings can have a central longitudinal axis that can extend at a first angle relative to a body of the access port cutter and a second opening of the plurality of openings can have a central longitudinal axis that can extend at a second angle relative to the body of the access port cutter that is different than the first angle. In some embodiments, the access port cutter opening can include a feature that can exert a force on the access port. In some embodiments, the access port can have a non-circular shape.

In yet another aspect, a surgical method can include inserting an access port body into an opening of an access port cutter, the access port cutter having a base portion with the opening, a blade, and an actuation mechanism. The method can include operating the actuation mechanism to linearly drive the blade along at least a portion of the base, and cutting the access port body by passing the blade linearly across the opening of the access port cutter.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Access port cutters and related methods are disclosed herein, e.g., for customizing a length of an access port to suit a particular patient and/or procedure at a point of use in a manner that can reduce risk of injury to both a user and the patient while maintaining integrity of the access port. Access port cutters of the present disclosure can include a base, a blade, and an actuation mechanism. The actuation mechanism can be configured to translate the blade linearly across an opening of the base such that the blade can cut through an access port received within the opening. As used herein, the phrase "cut through an access port" can mean cutting through an entire cross-section of a hollow body of the access port along a plane that can extend in a non-parallel orientation (i.e., oblique to or perpendicular to) a longitudinal axis of the access port. In other words, cutting through an access port can reduce a length of the access port as measured along the longitudinal axis of the axis port. Accordingly, access port cutters of the present disclosure can provide for an access port with a length tailored for a particular surgical procedure and can thereby reduce inefficiencies, e.g., inefficiencies associated with a longer port than necessary and/or with an unnecessary number of access ports prepared for a single procedure, in a safe and efficient manner.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Figure 1:
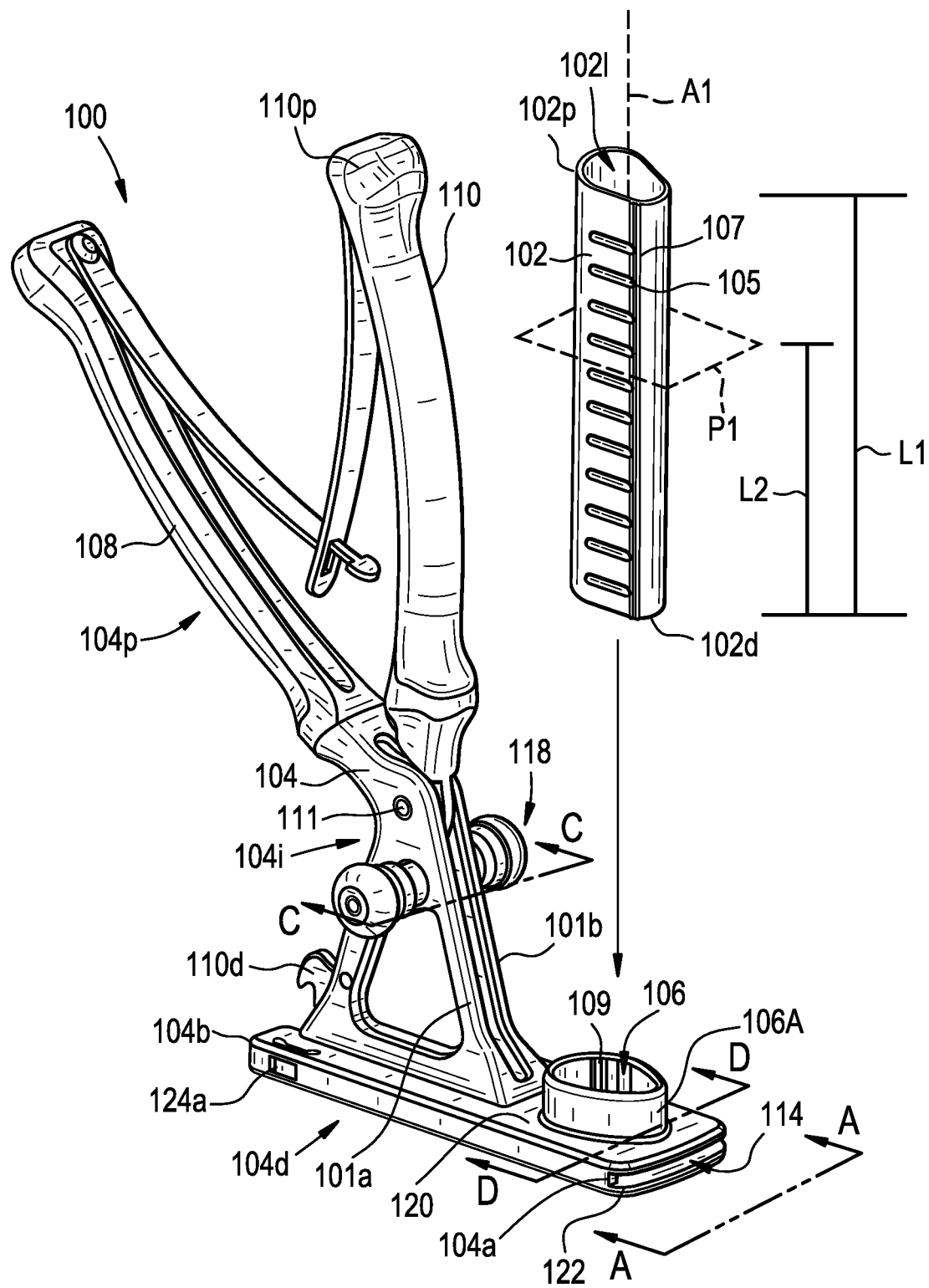
FIG. 1 is a perspective view of an embodiment of an access port cutter of the present disclosure and an embodiment of an access port that can be used therewith.

FIG. 1 illustrates one embodiment of an access port cutter 100 of the present disclosure. The access port cutter 100 can cut an access port 102 to a desired length as measured along a longitudinal axis A1 of the access port at a point of use, e.g., an operating room or surgical field, based on requirements of a particular surgical procedure and/or patient. The access port cutter 100 can have a base 104 with an opening 106. The opening 106 can be sized and shaped to receive the access port 102 along a longitudinal axis A2 (FIG. 4) of the opening. The base 104 can have a proximal portion 104p that can include a grip 108, an intermediate portion 104i that can have a first side 101a and a second side 101b with a gap 103 extending therebetween, and a distal portion 104d through which the opening 106 can extend. In some embodiments, an extension 106A can extend proximally from the distal portion 104d of the base and can surround at least a portion of the opening 106.

A handle 110 can have a proximal end 110p and a distal end 110d and can be movable relative to the base 104. A distal portion of the handle 110, including at least the distal end 110d, can extend through the gap 103 between the first and second sides 101a, 101b of the intermediate base portion 104i. In some embodiments, the handle 110 can pivot about a pivot pin 111 that can extend from the first side 101a of the intermediate base portion 104i through the handle 110 to the second side 101b of the intermediate base portion. The handle 110 can pivot such that movement of the proximal portion 110p of the handle away from a front end 104a of the base 104 causes the distal end 110d to move through the gap 103 towards the front end of the base. In some embodiments, the handle 110, the intermediate base portion 104i, and the proximal base portion 104p can extend perpendicular to the distal portion 104d of the base, i.e., can extend proximally from the distal portion of the base parallel to the longitudinal axis A2 of the opening 106. The handle 110 and the grip 108 can have an ergonomic design such that they can both be grasped by a user with either a right-hand or left-hand grip.

Figure 1A:
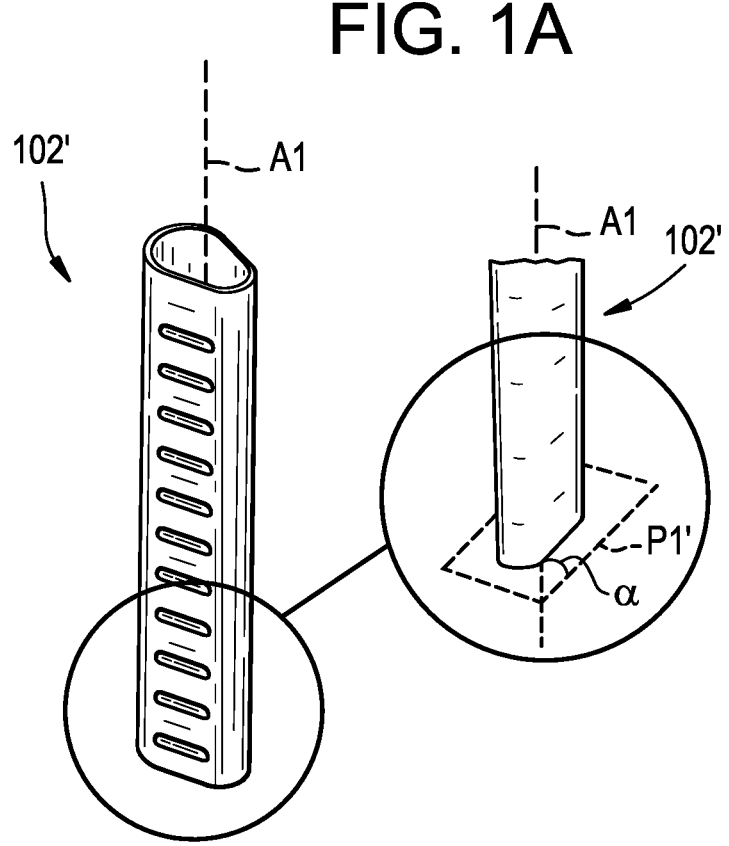
FIG. 1A shows one embodiment of an access port cut in accordance with the present disclosure.

As described in detail below, the handle 110 can form part of an actuation mechanism that can be configured to drive a blade 112 (FIG. 3) linearly within a channel 114 of the base 104 such that the blade traverses the opening 106 and can cut through the access port 102 received therein. The blade 112 can cut across or through an entire cross-section of the access tube 102 such that a length of the access tube as measured along a longitudinal axis A1 of the access tube can be reduced from an initial length L1 to a desired operating length L2. A safety feature, such as a lock pin 118, can prevent inadvertent actuation of the blade 112. In some embodiments, the blade 112 can cut the access port 102 along a cutting plane P1 that extends perpendicular to a longitudinal axis A1 of the access port. Turning to FIG. 1A, in other embodiments, the access port cutter 100 can cut an access port 102' along a cutting plane P1' that can extend at an oblique angle α relative to the longitudinal axis A1 of the access port 102'. In some such instances, the longitudinal axis A2 of the access port cutter opening 106 can be fixed at an oblique angle relative to a portion of the base 104 across which the blade 112 traverses to cut through the access port 102'. In other embodiments, the access port cutter 100 can include an adjustment feature that can allow a user to vary an angle at which the opening 106 extends relative to the base 104. In this manner, the access port cutter 100 can cut through the access port 102' such that a cut end of the access port can be angled to better conform to bony anatomy of a patient.

Returning to FIG. 1, the access port 102 can have a proximal end 102p and a distal end 102d with a lumen 102l extending therebetween. The initial length L1 of the access port 102 can be fixed, as measured along the longitudinal axis A1, from the proximal end 102p to the distal end 102d of the access port. While the access port 102 illustrated in FIG. 1 has an ovate or egg-shaped cross-section, the access port cutter 100 can be used with an access port having any of a variety of cross-sectional shapes, such as circular, triangular with rounded corners, etc. More particularly, a shape of the opening 106 of the access port cutter 100 can be formed with a complementary geometry to a geometry of an access port 102 intended to be used with the access port cutter 100.

In some embodiments, the access port 102 can include one or more engagement features, such as one or more slots 105 and/or ribs 107. For example, as shown in FIG. 1, the access port 102 can include a plurality of horizontal slots 105 that can be spaced apart along substantially the entire initial length L1 of the port (in some embodiments protruding ribs can be used in place of slots). The slots 105 can provide interface or engagement points for various surgical instruments during a surgical procedure and/or for alignment with a complementary feature (not shown) on an inner surface of the opening 106 and/or extension 106A of the access port cutter 100. In this manner, the slots 105 can be used to aid in aligning and securing the access port 102 within the opening 106. Additionally, or alternatively, the port 102 can include one or more vertical ribs 107 that can serve a similar purpose (in some embodiments a vertically-extending slot can be used in place of a rib). For example, the access port 102 can include a plurality of extruded vertical ribs 107 that can align with complementary or counterpart rib features extending from the inner surface of the opening 106 and/or extension 106A.

Figure 2:
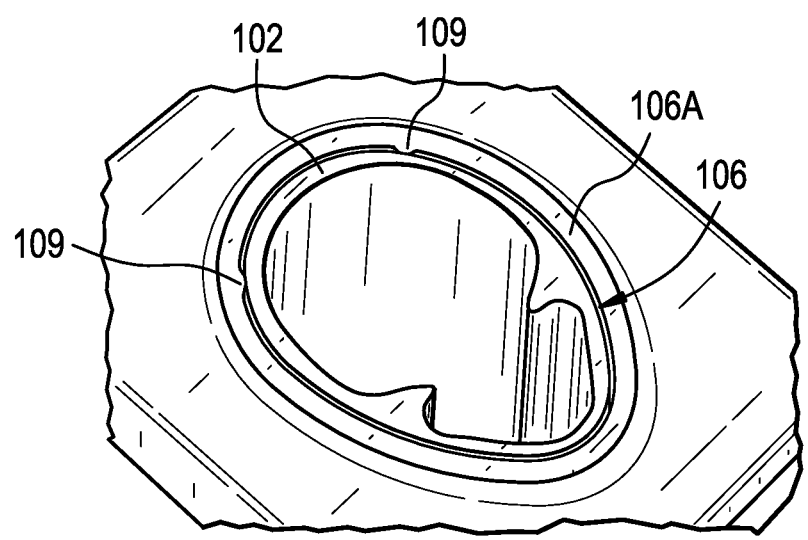
FIG. 2 is a partial cross-sectional view of the access port cutter of FIG. 1 taken along the line D-D of FIG. 1.

FIG. 2 is a partial cross-sectional view of the access port cutter 100 taken along the line D-D of FIG. 1, which shows the opening 106 and the extension 106A with the access port 102 received therein. The opening 106 and/or extension 106A can include one or more interference feature, such as ribs 109, that can extend toward the central longitudinal axis A2. The ribs 109 can exert a frictional force on the access tube 102 received within the opening 106 to create an interference fit which can hold the access port in place, both during and after a cut. Moreover, in some embodiments, the one or more ribs 109 can engage with counterpart ribs or slots 107 of the access port 102. While the illustrated embodiment of access port cutter 100 shows two ribs 109, a position and/or number of ribs can be varied. Additional or alternative interference features can include, for example, a spring, an elastomeric feature, a ball detent, etc., that can hold the access port 102 within the opening 106.

Returning now to the access port cutter 100, as mentioned above the blade 112 can be slidably received within the channel 114 of the base 104 such that the blade 112 can traverse the opening 106 and cut the access port 102. The channel 114 can extend along substantially an entire length of the distal base portion 104d from the first end 104a of the distal base portion to a second end 104b. The channel 114 can be formed between a proximal planar surface 120 and a distal planar surface 122. The opening 106 can be located towards the first end 104a of the distal base portion 104d and can extend through the planar surfaces 120, 122.

Figure 3:
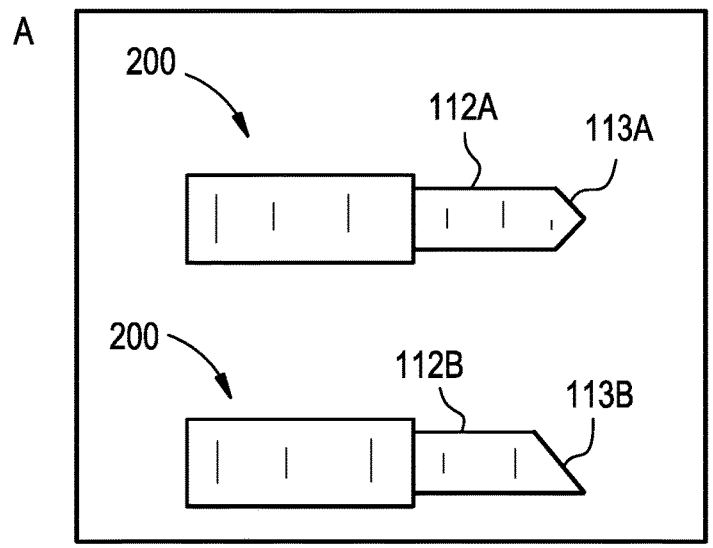
FIG. 3 is a cross-sectional view of the access port cutter of FIG. 1 taken along the line A-A of FIG. 1 with a blade cartridge received therein.
Figure 3:
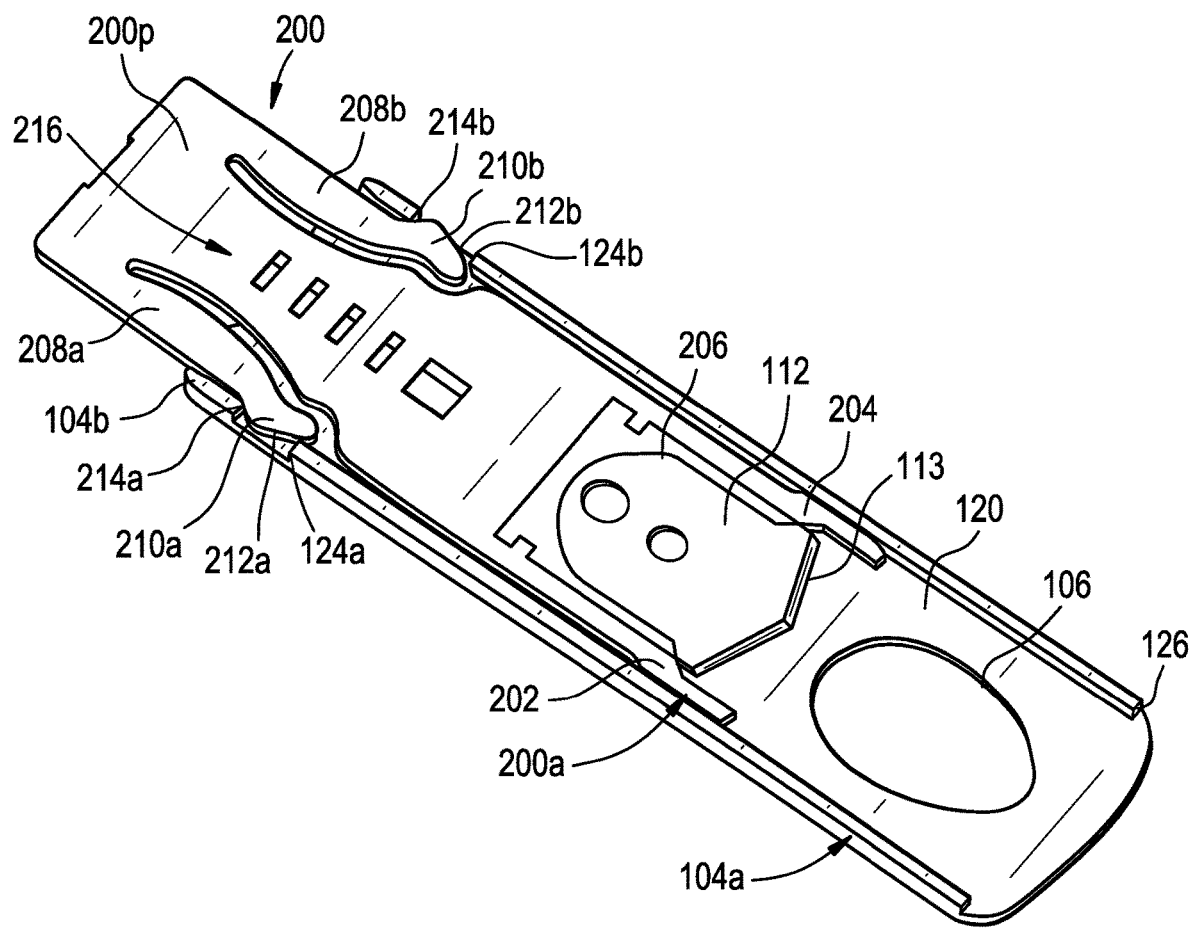

FIG. 3 is a cross-sectional view of the access port cutter 100 taken along the line A-A of FIG. 1 and shows the blade 112 slidably received within the channel 114 of the distal base portion 104d. In some embodiments, the blade 112 can be held within a blade cartridge 200 received within the channel 114. The cartridge 200 can have a generally planar body with a complementary shape to that of the channel 114. A first end 200a of the cartridge 200 can have a first arm 202 and a second arm 204 with a blade opening 206 extending therebetween. The blade 112 can be held within the cartridge 200 such that a leading cutting edge 113 of the blade 112 can be located within the blade opening 206. The blade opening 206 can align with the opening 106 of the base 104 such that the cutting edge 113 of the blade 112 can pierce and cut through the access port 102 received within the opening 106 of the base 104 as the cartridge 200 translates linearly within the channel 114 to the first end 104a of the base. In some embodiments, the blade 112 and a cut path of the blade can be designed such that deformation of the access port can be reduced. For example, the blade 112 can be placed such that a sharp tip of the blade can make first contact with, and pierce, the access port 102. In some embodiments, the blade 112 can be heated such that the blade can pass more smoothly through the access port 102. The first and second arms 202, 204 can extend a distance beyond the cutting edge 113 of the blade 112 such that, when the cartridge 200 is moved to its forward-most position i.e., to the first end 104a of the base 104, the cutting edge of the blade can remain recessed from a front edge 126 of the base. In this manner, the risk that a user can be cut by the blade 112 when the cartridge 200 and, accordingly, the blade 112 are in the forward-most position can be reduced.

In some embodiments, the blade 112 can be integrally formed with, or otherwise permanently attached to, the cartridge 200, as shown in FIG. 2, and the cartridge and blade can be disposable. Alternatively, the cartridge 200 can be reusable and the blade 112 can be inserted into the cartridge prior to operation of the access port cutter 100. For example, the blade 112 can be slid between the first arm 202 and the second arm 204 into the blade opening 206 of the cartridge 200.

The cartridge 200 can include one or more retention features, such as retention fingers 208*a*, 208*b*, that can hold the cartridge 200 in an initial or open position, i.e., a position in which the cutting edge 113 of the blade 112 can be remote from the opening 106 towards the back end 104*b* of the base, as shown, for example, in FIG. 3. In one embodiment, the retention fingers 208*a*, 208*b* can engage with openings 124*a*, 124*b* in the distal base portion 104*d*. The fingers 208*a*, 208*b* can be biased outward such that a tip 210*a*, 210*b* of the fingers 208*a*, 208*b* can extend into the opening 124*a*, 124*b*. The tip 210*a*, 210*b* can include a ramped edge 212*a*, 212*b* that can slope inward towards a forward-most point of the tip. In this manner, a forward force can be applied to the cartridge 200 such that the bias of the fingers 208*a*, 208*b* can be overcome and the tip 210*a*, 210*b* can slide forward and inward from the openings 124*a*, 124*b* along the ramped edge 212*a*, 212*b*. The cartridge 200, with the blade 112, can translate along the channel 114 towards the first end 104*a* of the base.

The tip 210*a*, 210*b* of the finger 208*a*, 208*b* can also ensure that the cartridge 200 can only be inserted into the channel 114 in one direction, i.e., with the cutting edge 113 of the blade 112 facing forward towards the first end 104*a* of the base 104. For example, the tip 210*a*, 210*b*, can include a second ramped surface 214*a*, 214*b* that can slope outwards away from a central longitudinal axis of the cartridge 200. The ramped surface 214*a*, 214*b* can abut the second end 104*b* of the base 104 if the cartridge 200 is inserted in the wrong direction and can prevent the cartridge from being further inserted into the channel 114. In some embodiments, the cartridge 200 can have a symmetrical design with an identical proximal-facing surface 200*p* and distal-facing surface (not shown). Moreover, as shown in insert A, in some embodiments the blade 112A received within the cartridge 200 can have a symmetrical cutting edge 113A with an upper taper and a lower taper coming together at a blade tip, which can allow the blade 112A to cut through the access port 102 with either side of the blade facing proximally. Accordingly, the cartridge 200 can be loaded into the base 104 with either side facing towards the proximal planar surface 120, which can simplify the loading process. In other embodiments, the cartridge can be designed such that a certain face must face towards the proximal planar surface for proper loading. This can be useful for embodiments that utilize a blade 112 with a cutting edge 113 having a single-taper geometry. For example, as shown in insert A, a blade 112B can have a cutting edge 113B with an upwards or proximal taper from the blade tip. This blade design can be beneficial to urge debris from the access port 102 and the cut portion of the access port upwards, away from a patient.

Figure 4:
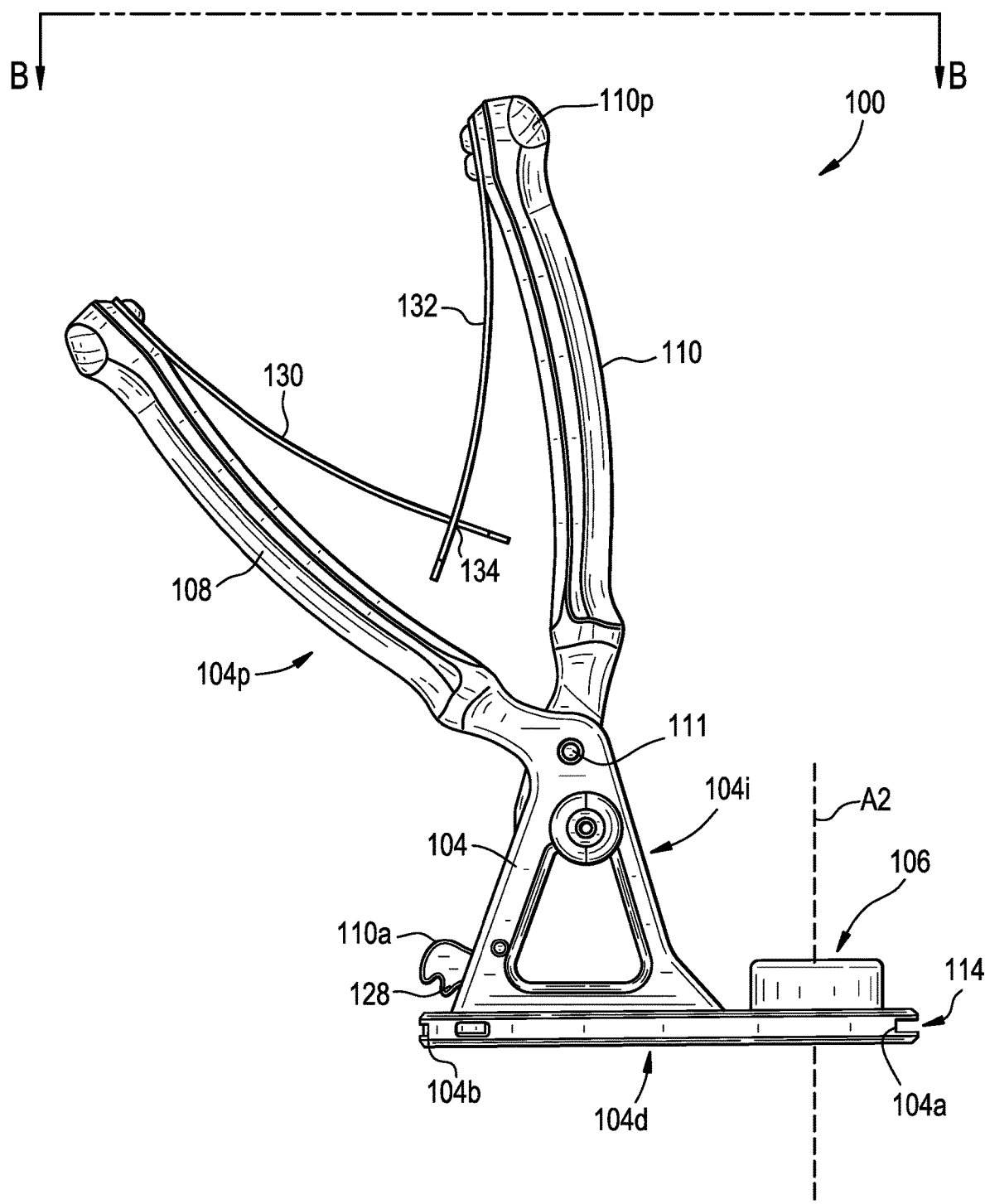
FIG. 4 is a side view of the access port cutter of FIG. 1.
Figure 5:
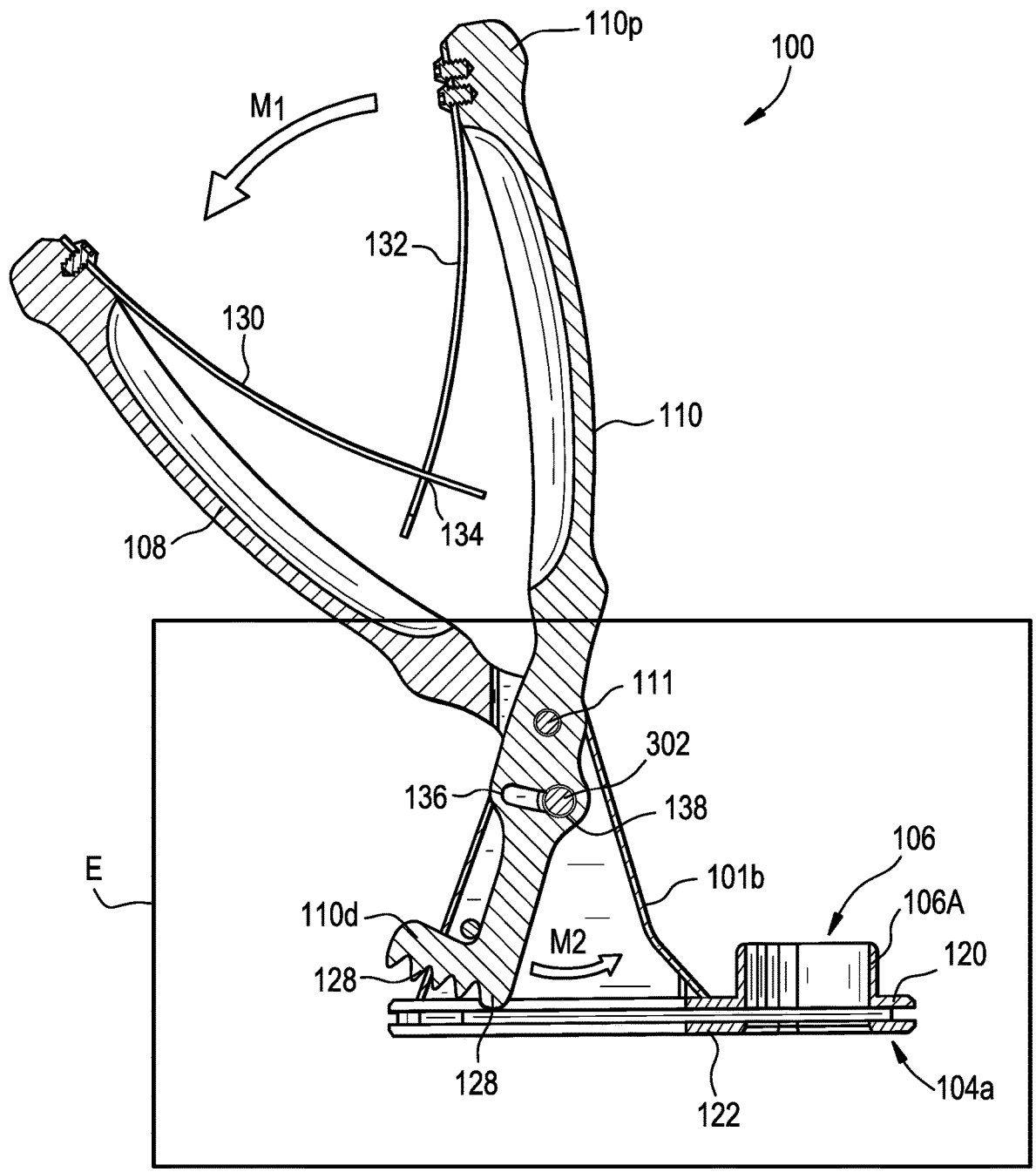
FIG. 5 is a cross-sectional view of the access port cutter of FIG. 1 taken along the line B-B of FIG. 4.
Figure 9:
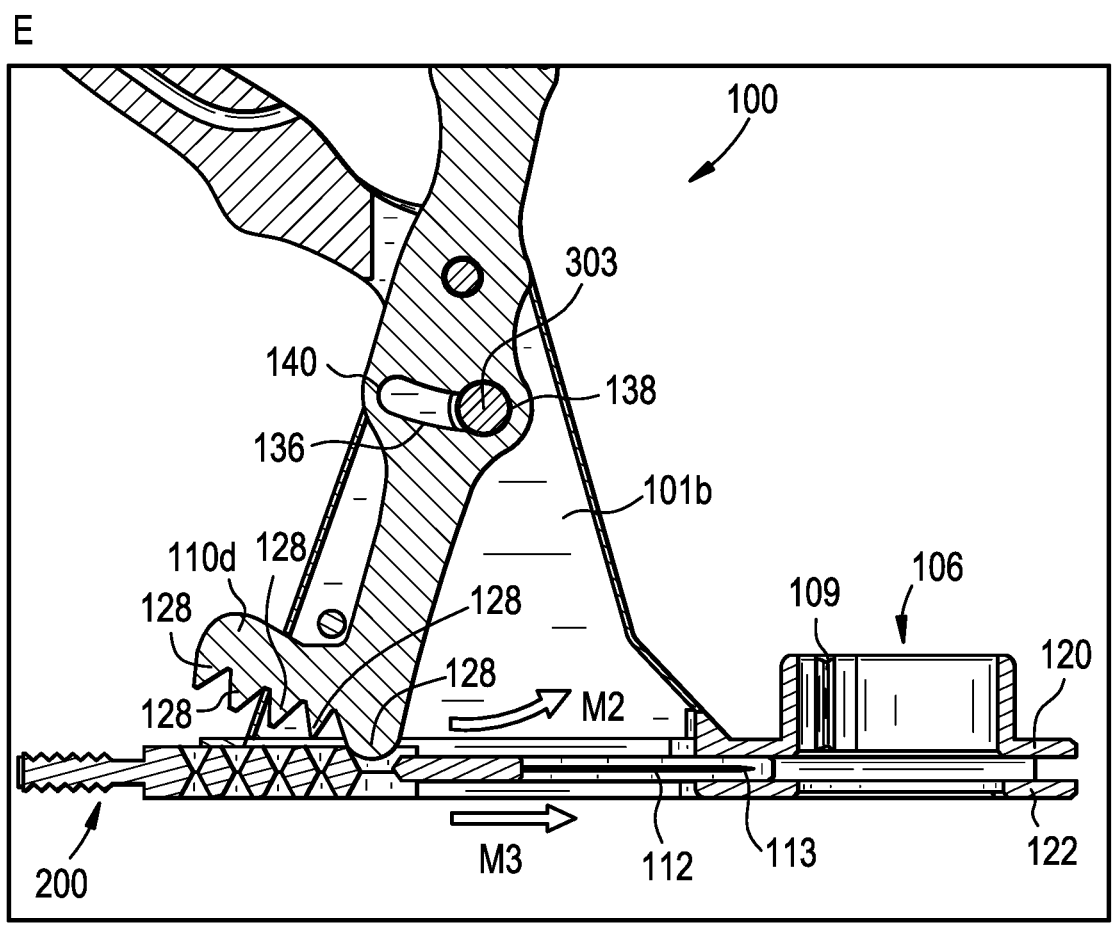
FIG. 9 is an enlarged side view of a portion of the access port cutter shown in box E of FIG. 5.
Figure 10:
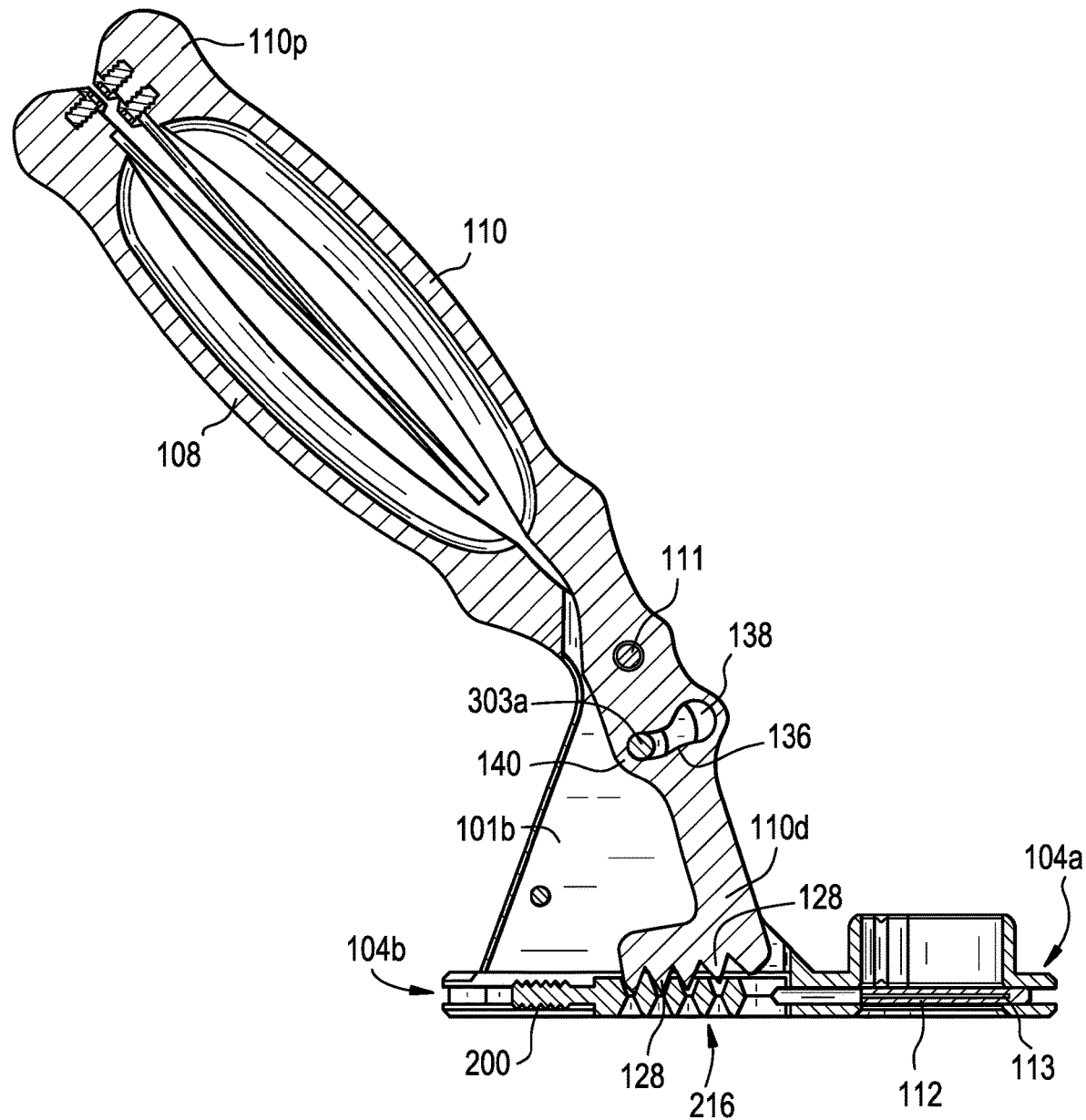
FIG. 10 shows the cross-sectional view of FIG. 5 with the access port cutter in a final position.

FIG. 4 shows a lateral view of the access port cutter 100 in an initial or open position in which the proximal portion 110*p* of the handle 110 can be located in a forward-most position. FIG. 5 shows a cross-sectional view of the access port cutter 100 taken along the line B-B of FIG. 4. As introduced above, the handle 110 can be pivotably connected to the base 104 about the pivot point 111 such that rotational movement M1 of the proximal end 110*p* of the handle away from the first end 104*a* of the base, e.g., towards the grip 108, can cause the distal end 110*d* of the handle to move towards the first end 104*a* of the base 104, e.g., in the direction of the arrow M2. The distal end 110*d* of the handle can engage with the blade 112 and/or cartridge 200 such that rotational movement in the direction M2 of the distal end can cause the blade to linearly translate along the channel 114 towards the opening 106 in the direction M3 (FIG. 9). In some embodiments, rotational motion of the handle 110 can be transferred to linear motion of the blade 112 through, for example, a rack-and-pinion type mechanism. More particularly, one or more teeth 128 can be formed on the distal end 110*d* of the handle 110. The teeth 128 can engage with a rack 216 formed in the cartridge 200 such that the rotational motion M2 of the teeth 132 can translate into linear motion M3 of the cartridge 200 (FIGS. 9 and 10). In other embodiments, motion of the handle 110 can be transferred to linear motion of the blade 112 through another form of linear actuation mechanism, e.g., a ratcheting mechanism. In some embodiments, a link 128, 130 can extend distally from the grip 108 and the handle 110, respectively. The links 128, 130 can couple at a connection point 134 and can provide resistance to movement of the handle 110 relative to the grip 108 such that a force on the handle 110 is required to overcome the resistance and move the proximal portion of the handle towards the grip. Accordingly, the links 128, 130 can reduce the risk of injury and/or inadvertent actuation of the blade 112.

Figure 6:
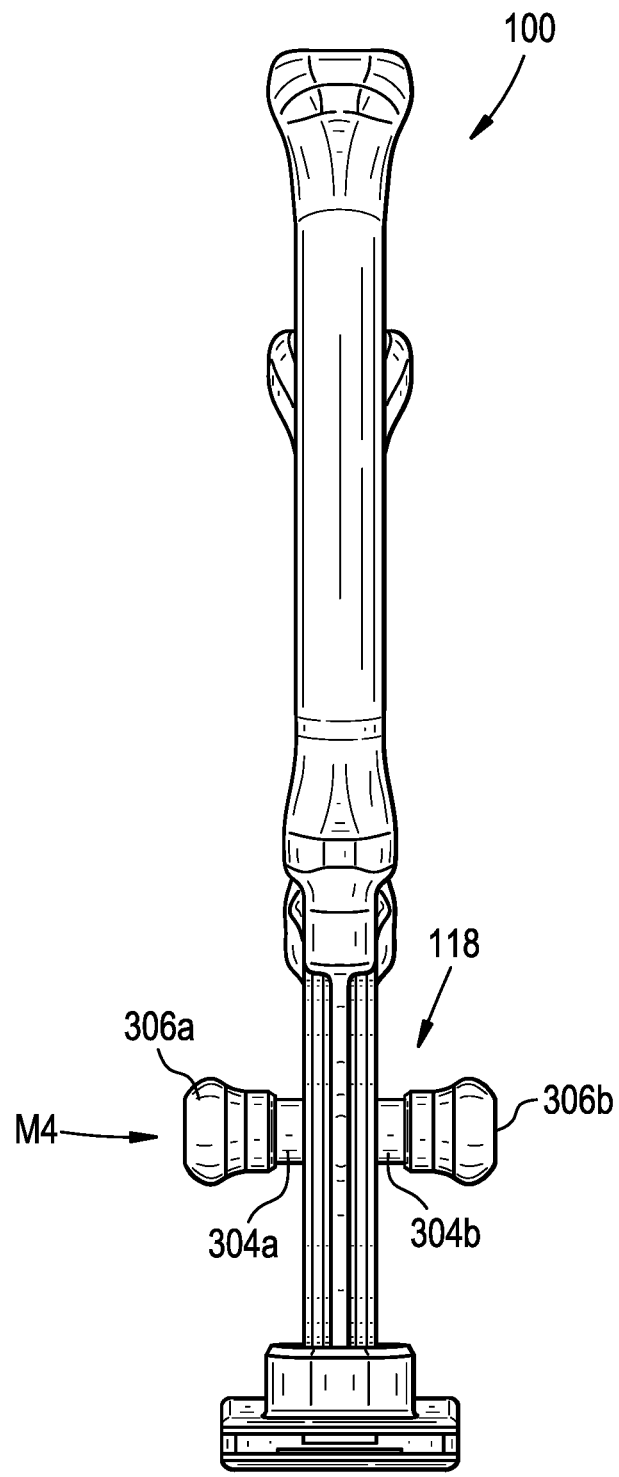
FIG. 6 is a front view of the access port cutter of FIG. 1.
Figure 7:
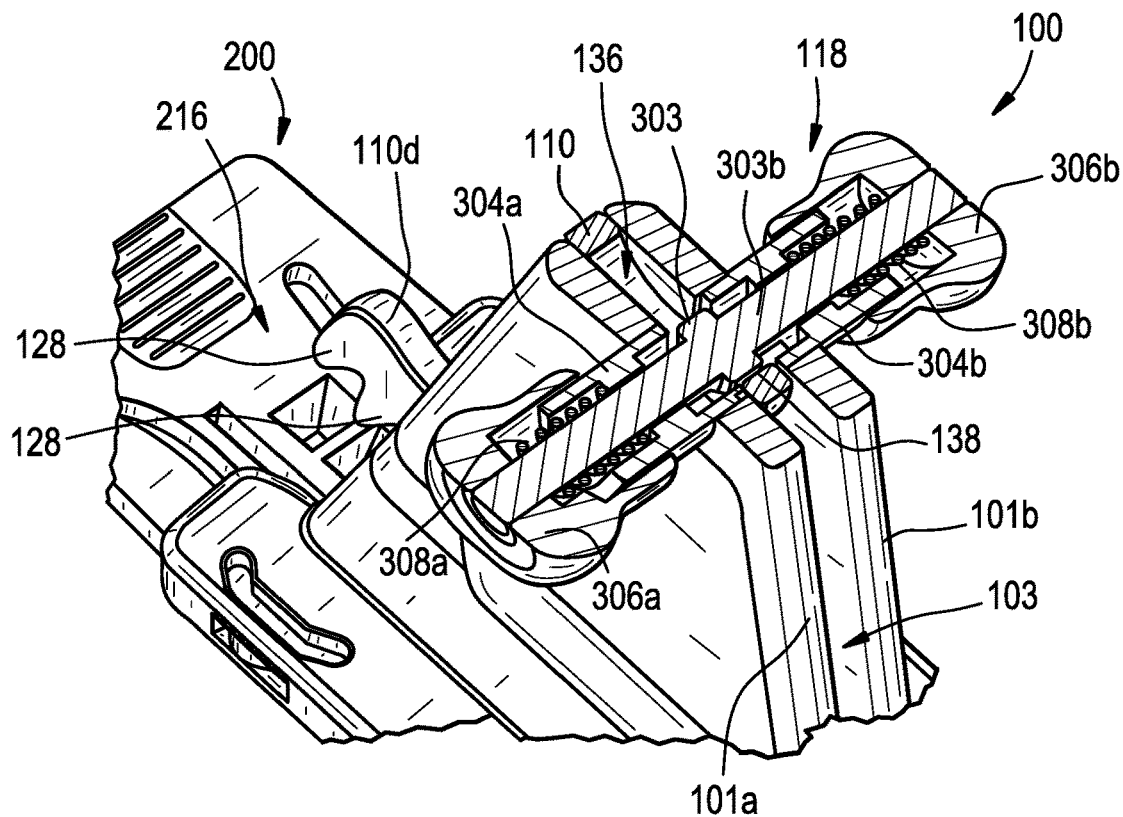
FIG. 7 is a cross-sectional view of the access port cutter of FIG. 1 taken along the line C-C of FIG. 1 with a lock in a first position.
Figure 8:
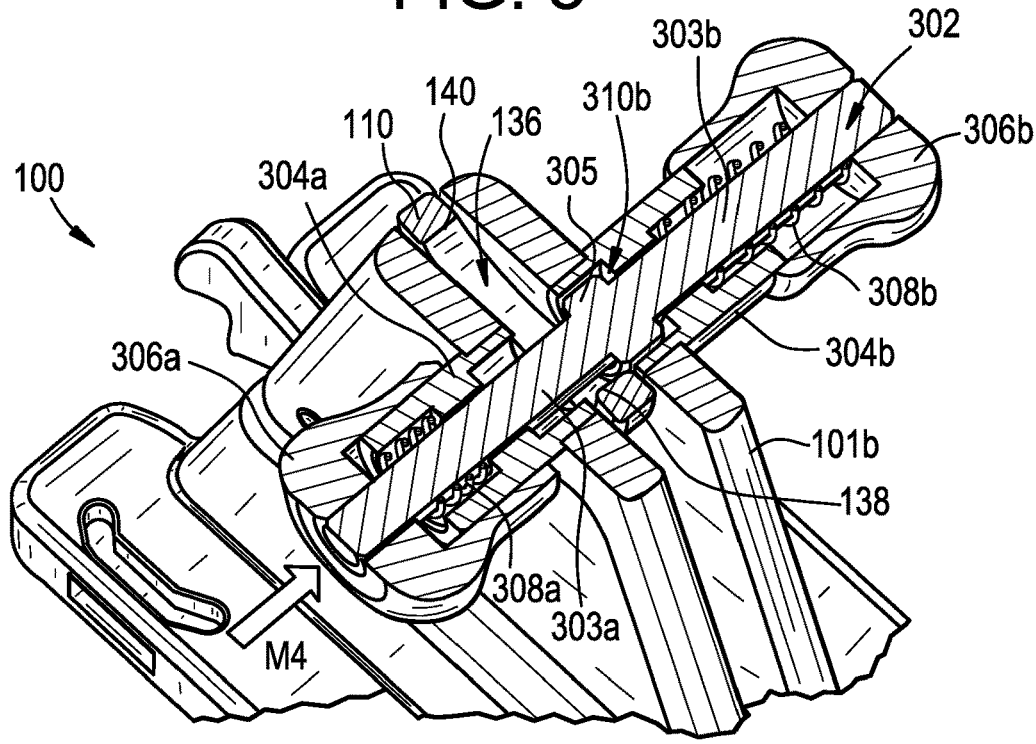
FIG. 8 shows the cross-sectional view of FIG. 7 with the lock in a second position.

A safety lock feature, such as the bi-directional lockout pin 118 (also referred to herein as the lock) will now be described in detail with reference to FIGS. 6-8. FIG. 6 shows a front view of the access port cutter 100 of FIG. 1, with the lock 118 in a first position in which relative motion between the handle 110 and the base 104 can be restricted. The lock 118 can require that a user take a deliberate action before the blade 112 can be driven by the access port cutter 100. For example, a user can be required to actuate the lock 118 to move the lock from the first position shown in FIG. 6 to a second position in which the handle can move, i.e., pivot, relative to the base. FIG. 7 is a cross-sectional view of the access port cutter 100 taken along the line C-C of FIG. 1, which shows a cross-sectional view of the lock 118 in the first position where movement of the handle 110 is restricted. FIG. 8 shows the same cross-sectional view as FIG. 7, but with the lock 118 in the second position where movement of the handle 110 is permitted.

The lock 118 can include a pin 302, a first intermediate portion 304*a* received through the first side 101*a* of the intermediate base portion 104*i*, a second intermediate portion 304*b* received through the second side 101*b* of the intermediate base portion, a first outer portion 306*a*, and a second outer portion 306*b*. The pin 302 can be coupled to the first outer portion 306*a* and the second outer portion 306*b* and can extend from the first outer portion, through the first intermediate portion 304*a*, across the gap 103 of the intermediate base portion 104*i*, through the second intermediate portion 304*b* to the second outer portion 306*b*. The pin 302 can have an enlarged diameter portion 303 with reduced diameter portions 305*a*, 305*b* extending from either side of the enlarged diameter portion. In some embodiments, the enlarged diameter portion 303 can be centrally located along a longitudinal axis of the pin 302. The pin 302 can extend across the gap 103 of the intermediate base portion 104*i* through a slot 136 (FIG. 5) of the handle 110. The slot 136 can have an arcuate shape with an enlarged diameter portion 138 at a first end thereof.

With reference to FIGS. 7 and 8, a first spring 308a can be placed between the first outer portion 306a and the first intermediate portion 304a and a second spring 308b can be placed between the second outer portion 306b and the second intermediate portion 304b. In the first position, the first and second springs 308a, 308b can exert opposing forces on the first and second outer portions 306a, 306b such that the central pin 302 can be held with the enlarged diameter portion 305 of the pin extending through the enlarged diameter portion 138 at the first end of the slot 136 in the handle 110. Accordingly, motion of the handle 110 relative to the base 104 can be prevented as the enlarged diameter portion 303 of the pin 302 can have a diameter larger than that of the remaining portion of the slot 136 such that motion of the slot can be blocked by the pin 302. A force M4 (e.g., a compressive force on one side of the base 104 or a tension force on an opposite side thereof) can be applied to one of the first and second outer portions 306a, 306b to move the lock 118 from the first position into the second position.

For example, FIG. 8 shows the lock 118 in the second position with a compressive force M4 having been applied to the first outer portion 306a, which can compress the first spring 308a and translate the pin 302 towards the second intermediate portion 304b. More particularly, in the second position, the enlarged diameter portion 303 of the pin 302 can be received within a recess 310b of the second intermediate portion 304b and the reduced diameter portion 305a of the pin can extend through the enlarged diameter portion 138 of the slot 136 in the handle 110. The reduced diameter portion 305a of the pin 302 can have a diameter less than or equal to the diameter of the slot 136 such that the slot can move relative to the pin, which can thereby allow motion of the handle 110 relative to the base 104. Alternatively, the compressive force M4 can be applied to the second outer portion 304b such that the lock 118 can be placed in the second position with the enlarged diameter portion 303 received within a recess 310a of the first intermediate portion 304a and the reduced diameter portion 305b extending through the enlarged diameter portion 138 of the slot 136.

FIG. 9 shows an enlarged view of the portion of the access port cutter 100 shown in the box E of FIG. 5 with the cartridge 200 received within the distal portion 104d of the base 104. More particularly, the cartridge 200 can be received within the channel 114 in the initial or open position in which the cutting edge 113 of the blade 112 can be remotely located from the opening 106 towards the back end 104b of the base. In the initial position of the access port cutter 100, a forward-most tooth 128 of the distal end 110d of the handle 110 can engage with a corresponding portion of the rack 216 of the cartridge 200. The lock 118 can be placed in the first position such that the enlarged diameter portion 303 of the pin can be received within the enlarged diameter portion 138 of the slot 136. Accordingly, the lock 118 can restrict movement of the access port cutter 100 and the cartridge 200.

FIG. 10 shows the access port cutter of FIG. 5 with the cartridge 200 received within the distal end 104d of the base 104 in a final or closed position, i.e., a position in which the handle 110 has been moved such that the blade 112 can extend across the opening 106 and the cutting edge 113 of the blade can be located beyond the opening 106 towards the base's first end 104a. In the closed position of FIG. 10, the lock 118 can be in the second position such that the reduced diameter portion 303a of the pin 302 can be received within the slot 136 of the handle 110, and can abut a second end 140 of the slot 136. The proximal portion 110p of the handle 110 can extend towards the back end 104b of the base and the distal portion 110d of the handle can extend towards the front end 104a of the base. The teeth 128 can be engaged with a back portion of the rack 216 of the cartridge 200 as the cartridge translated towards the front end 104a of the base.

One embodiment of a method of operating the access port cutter 100 to cut the access port 102 will now be described with reference to FIGS. 1-10. The access port cutter 100 can be placed in the initial or start position which can prepare the access port cutter for use in a safe manner. The lock 118 can be placed in the first position in which movement of the handle 110 relative to the base 104 is restricted. The cartridge 200 can be placed and secured within the channel 114 of the distal base portion 104d such that the cutting edge 113 of the blade 112 is remote from the opening 106. In some embodiments, a user (e.g., a surgeon, nurse, surgical robot, etc.) can insert the cartridge 200 into the back-end 104b of the channel 114 and can slide the cartridge forward towards the front-end 104a of the channel until one or more engagement features of the cartridge (e.g., tips 210a, 210b) of the retention fingers 208a, 208b) engage with counterpart engagement features of the access port cutter (e.g., openings 124a, 124b of the distal base portion 104d). In instances in which the blade 112 requires insertion into the cartridge 200, e.g., where the cartridge is reusable and the blade disposable, the user can slide the blade into the blade opening 206 of the cartridge until the blade is securely received therein prior to inserting the cartridge into the channel 114 of the access port cutter 100. In other embodiments, the blade 112 can be directly loaded into the channel 114 without use of the cartridge 200. In such embodiments, the blade 112 can include one or more engagement features (e.g., retention fingers) formed directly thereon such that the blade can similarly be secured within the channel 114 in the initial position. Accordingly, the access port cutter 100 can be placed in the initial position in which the blade 112 can be located remote to the opening 106 and movement of the handle 110 and the blade 112 relative to the base 104 restricted.

The access port 102 having the initial length L1 can be inserted through the opening 106 of the access port cutter 100 until a desired length L2 extends distally from the opening 106. More particularly, the access port 102 can be received within the opening 106 such that the desired length L2 can extend distally from the distal planar surface 122 of the base 104. The desired length L2 can be determined based on any number of factors, such as a surgical procedure to be performed, an access approach of the surgical procedure, patient anatomy, patient Body Mass Index, surgical instruments to be used in the procedure, etc. In some embodiments, the access port 102 can be inserted distally along the axis A2 into the opening 106 (i.e., top-loaded), as shown in FIG. 1. Alternatively, the access port 102 can be inserted proximally along the axis A1 into the opening (i.e., bottom-loaded). In some embodiments, the distal end 102d of the access port 102 can be inserted through an incision in a patient to a prior to inserting the proximal end 102p of the access port proximally into the opening 106 of the access port cutter 100. As discussed above, in some embodiments, the access port 102 can be received within the access port cutter opening 106 such that one or more engagement features of the access port e.g., one or more horizontal slot 105 and/or vertical rib 107, can engage with one or more counterpart features of the opening 106 (not shown). Further, in some embodiments, the access port 102 can be inserted such that the one or more friction features of the extension 106A, e.g., ribs 109, can exert a force on the access port 102 that can aid in retaining the access port within the opening.

The lock pin 118 can be moved from the first position to the second position to place the access port cutter 100 in a configuration to allow movement of the handle 110 relative to the base 104. More particularly, in some embodiments, a user can push or otherwise exert a force M4 on the first outer portion 306a in an axial direction of the central pin 302 (see FIG. 7). The force M4 can compress the spring 308a and can move the first outer portion 306a towards the intermediate base portion 104i such that the pin 302 can move in the direction of the compressive force from the first position in which the enlarged diameter portion 303 of the pin extends through the slot 136 of the handle 110 (see FIG. 6 and FIG. 9) to the second position in which the reduced diameter portion 305a of the pin extends through the slot of the handle (see FIG. 7). While discussion herein references a compressive force M4 as applied to the first outer portion 306a, the compressive force can alternatively be applied to the second outer portion 306b, which can similarly move the lock 118 from the first position to the second position. Still further, tension forces can be applied rather than compression forces to achieve the same effect.

With the lock 118 in the second position, the proximal portion 110p of the handle 110 can be pivoted relative to the base 104 such that the distal end 110d of the handle can cause the blade 112 to linearly translate along the channel 114 towards the opening 106. The proximal portion 110p of the handle 110 can be moved towards the grip 108 with the rotational motion M1 such that the handle can pivot about pivot point 111 relative to the base 104. As the handle 110 pivots, the slot 136 can move along the reduced diameter portion 305a of the central pin 302, and the distal end 110d of the handle 110 can rotate along the arc M2 such that the one or more teeth 128 can sequentially come into contact with portions of the rack 216 of the cartridge 200. As the teeth 128 engage and disengage with counterpart portions of the rack 216, the rotational motion M2 of the distal end 110d of the handle can be transferred into the linear forward motion M3 of the cartridge 200 and, accordingly, the blade 112 (see FIG. 9).

The handle 110 can be pivoted relative to the base such that the blade 112 can translate within the channel 114 towards the front end 104a of the base and the cutting edge 113 of the blade can traverse the opening 106 (see FIG. 10). Accordingly, the blade 112 can cut through the access port 102 received within the opening 106 and can thereby reduce the axial length of the access port to the desired length L2. The handle 110 can be pivoted to the final position (FIG. 10) in which the second end 140 of the slot 136 can abut the central pin 302 of the lock 118. In the final position, the blade 112 can extend across the opening 106 and the cutting edge 113 of the blade can be located beyond the opening towards the front end 104a of the base 104. The blade 112 can effectively prevent debris from the access port 102, i.e., a portion of the access port that extends proximal to the cutting plane P1, from falling distally through the opening 106. In some embodiments, the cutting edge 113 of the blade 112 can taper upwards which can urge debris away from the patient. Moreover, in some embodiments, the ribs 109 of the extension 106A can retain the cut-off portion of the access port 102 and any cut debris such that the risk of debris falling into the surgical site and/or onto the patient can be reduced. Further, the access port 102 can be made from a non-brittle material such that debris fragments can be reduced upon cutting through the access port.

Figure 11:
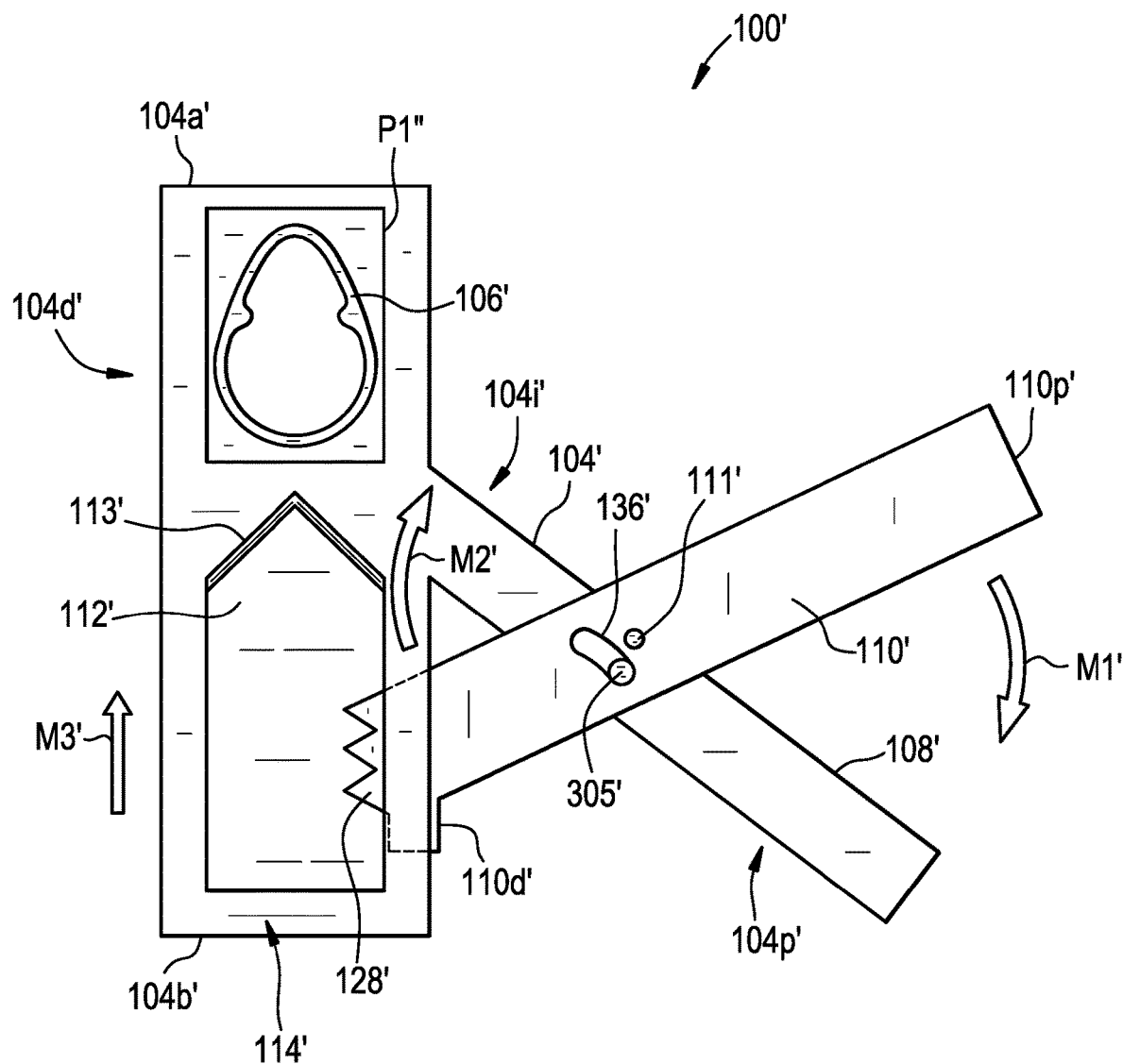
FIG. 11 is a cross sectional view of another embodiment of an access port cutter of the present disclosure.

FIG. 11 shows a top view of a cross-section of another embodiment of an access port cutter 100' with the cross-section taken along a cutting plane P1''. Except as indicated below, the structure, operation, and use of this embodiment is similar or identical to that of the access port cutter 100, with like-numbered components generally having similar features. Accordingly, description of the structure, operation, and use of such features is omitted herein for the sake of brevity. The access port cutter 100' can include a base 104' with an opening 106'. The opening 106' can receive an access port 102 (FIG. 1) along a longitudinal axis (not shown) that can extend normal to the page of the figure, i.e., into and out of the page in the view of FIG. 11. The base 104' can have a proximal portion 104p' that can include a grip 108', an intermediate portion 104i' that can have a first side 101a' and a second side (not shown) with a gap extending therebetween, and a distal portion 104d' with the opening 106' extending therethrough. The distal portion 104d' can have a distal planar component 122', a proximal planar component (not shown), and a channel 114' extending therebetween. The cross-sectional view of FIG. 11 can be taken along the channel 114'. A blade 112' can be slidably received within the channel 114'. In some embodiments, the blade 112' can be held by a cartridge 200 (FIG. 3) that can be placed within the channel 114' as described above. The access port cutter 100' can include a handle 110' that can pivot relative to the base 104' about a pivot point 111'. The handle 110' can engage with the cartridge 200 and/or blade 112' such that rotational movement M2' of the distal end 110d' of the handle can cause forward linear motion M3' of the blade towards the opening 106'.

In the embodiment of FIG. 11, the intermediate base portion 104i', the proximal base portion 104p', the grip 108', and the handle 110' can extend from the distal base portion 104d' perpendicular to the longitudinal axis A1 of the opening 106'. Put another way, these portions 104i', 104p', 108', and 110' can extend from the distal base portion 104d' in-line with the cutting plane P1''. The access port cutter 100' can further include any of the features or components described above. For example, the access port cutter 100' can include a lock 118 that can engage with a slot 136' of the handle 110'. The distal end 110d' of the handle 110' can include one or more teeth 128' that can engage with a counterpart rack 216 on the cartridge 200 (FIG. 3). Operation of the access port cutter 100' can be similar or identical to that of the access port cutter 100, described above. While the embodiments of the access port cutters 100, 100' described above can have a handle 110, 110' and a grip 108, 108' that can extend at fixed angles relative to the distal base portion 104d, 104d', in other embodiments, the handle and the grip can be adjustable such that an angle at which they extend relative to the distal base portion can be varied. In some embodiments, the handle 110, 110' and the grip 108, 108' can extend at a fixed angle, or can be adjusted to a particular angle, relative to the distal base portion 104d, 104d' such that the handle and grip can extend away from a patient while operating the access port cutter over or near the patient. Accordingly, a user can cut the access port 102 at a point of use without contacting the patient.

FIGS. 12-40 illustrate alternative embodiments of access port cutters of the present disclosure. Each access port cutter can include a blade that can linearly translate along at least a portion of a base and can traverse an opening and cut an access port tube received therein. Moreover, each of the access port cutters of FIGS. 12-40 can include a single blade that can be actuated at a point of use, e.g., at a surgical site, in a surgical field, near a patient, etc. The access port cutters can be used to customize or tailor the access port to a desired length based on particular needs of a patient and/or surgical procedure. While many of the access port cutters described throughout the present disclosure are generally discussed as being hand-held or operable by hand, in some embodiments, such access port cutters can be mounted to a table or reusable case/tray. Further, in some embodiments, such access port cutters can be navigated instruments and can be operated by a robot in the context of a robotic or robot-assisted surgical procedure.

Figure 12:
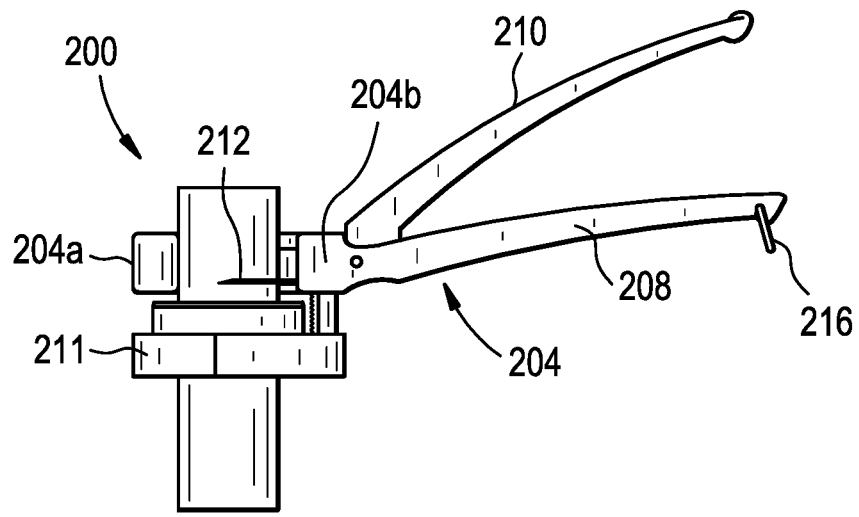
FIGS. 12-40 illustrate various embodiments of access port cutters in accordance with the present disclosure.
Figure 13:
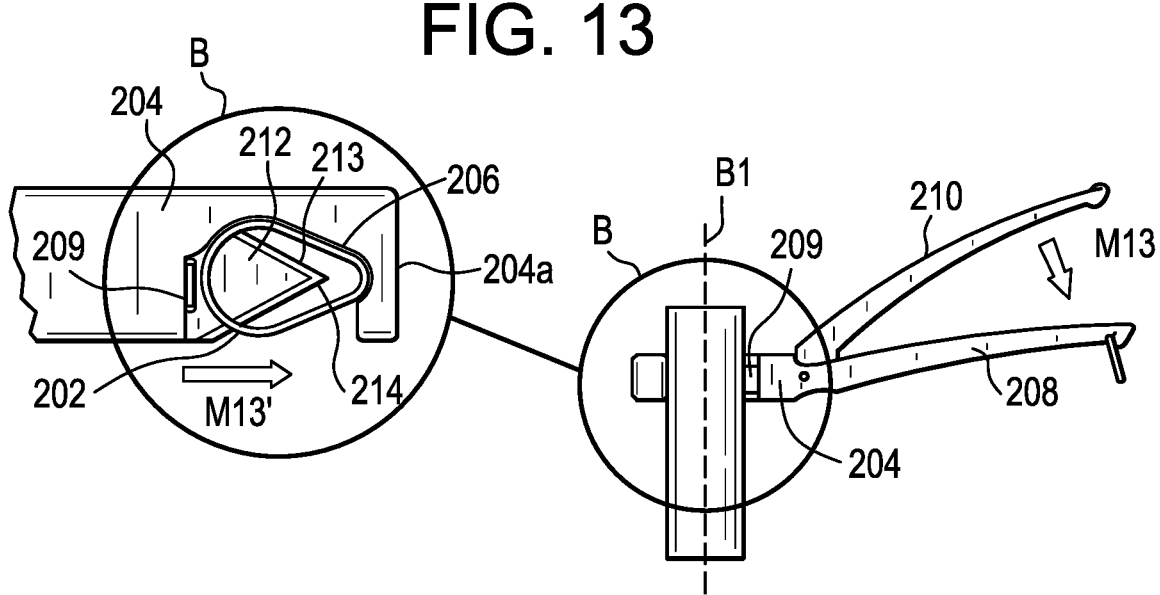

FIGS. 12 and 13 show an access port cutter 200. The access port cutter 200 can include a base 204 with an opening 206 and a grip 208. The opening 206 can receive an access port 202 along a longitudinal axis B1 of the opening. A handle 210 can pivot relative to the base 204 and can linearly drive a blade 212 from a back end 204*b* of the base towards a front end 204*a* of the base across the opening 206. The handle 210 can be vertically or substantially vertically (i.e., in the direction of the longitudinal axis B1) aligned with the grip 208 such that the handle can pivot vertically relative to the base 204. A vertical orientation of the handle 210 can limit torque on the access port 202 when the handle 210 pivots relative to the base 204. In some embodiments, the access port cutter 200 can couple with an access port anchor 211 which can aid in maintaining a proper alignment of the access port 202 relative to the access port cutter.

FIG. 13 is a lateral view of the access port cutter 200 and the insert B is a top-view taken along the axis B1 of the portion of the access port cutter 200 shown in circle B. In some embodiments, the opening 206 can be U-shaped or substantially U-shaped such that the access port 202 can be inserted laterally with respect to the longitudinal axis B1 (i.e., side-loaded) into the opening 206. In other embodiments, the access port 202 can be inserted longitudinally along the axis B1. The access port cutter 200 can include a protrusion 209 that can extend from a portion of the base 204 towards the opening 206. The protrusion 209 can exert a friction force on the access port 202 received within the opening 206 and can aid in retaining the access port therein. For example, the protrusion 209 can be a leaf spring that can hold a debris portion of the access port 202 after the access port is cut by the blade 212. In some embodiments, the opening 206 can be dimensioned such that a non-cylindrical access port 202 can be received and held therein.

The handle 210 can be moved towards the grip 208 in a direction M13, which can cause the blade 212 to translate linearly along a cut path M13' towards a front end 204*a* of the base 204 and traverse the opening 206. In some embodiments, the blade 212 and the cut path M13' can minimize deformation of the access port 202. For example, the blade 212 can come to a sharp tip 214 at a forward-most end. The opening 206 can be designed to receive the access port 202 such that a weak point of the access port can be placed at a location at which the sharp tip 214 of the blade 112 can first contact the access port 202 as the blade 112 moves along the cut path M13'. In some embodiments, the blade 212 can lock into the front end 204*a* of the base 204 after a cut. For example, a lock, such as a latch 216, can extend from the grip 208 and can be configured to engage with the handle 210 to lock the handle, and, accordingly, the blade 212 in a final cut position. Locking the blade 212 following the cut captures debris from the access port 202 and can reduce the risk of injury to a user from the cutting edge 213 of the blade 212. The access port cutter 200 and debris, if captured, can then be removed in one step from the point of use.

Figure 14:
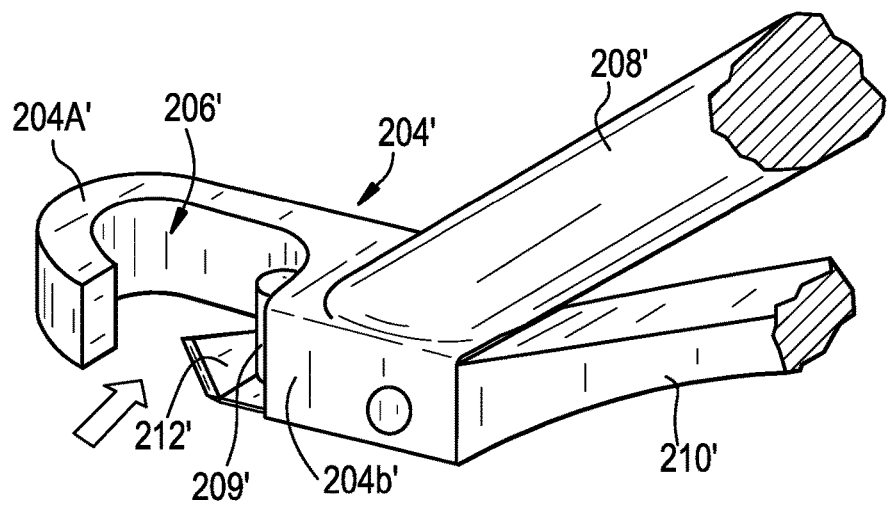
Figure 15:
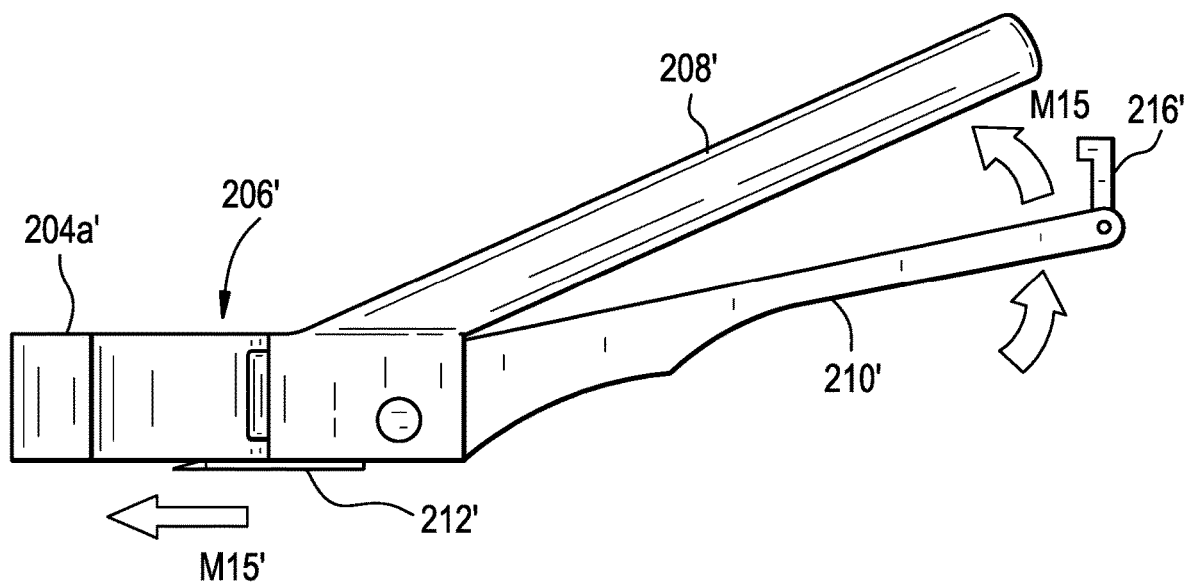

FIGS. 14 and 15 show another embodiment of an access port cutter 200' that is a variation of the access port cutter 200 of FIGS. 12 and 13. Accordingly, except as indicated below, the structure, operation, and use of this embodiment is similar or identical to that of the access port cutter 200, with like-numbered component generally having similar features. The access port cutter 200' can include a base 204' with an opening 206' and a grip 208'. A handle 210' can move relative to the base 204' to linearly drive a blade 212' across the opening 206'. The opening 206' can include a protrusion 209' which can both hold the access port when initially positioned within the opening and retain a cutoff portion of the access port and any cut debris within the opening following use. In the illustrated embodiment, the handle 210' can be moved proximally towards the grip 208' in the direction M15. In other words, a user can squeeze the handle 210' upwards towards the grip 208' which can cause the blade 212' to extend from the back-end 204*b*' of the base 204' towards the front end 204*a*' across the opening 206' along a cut path M15'. A lock 216' can extend from the handle 210' and can engage with the grip 208' to lock the handle to the grip in the final cut position.

Figure 16:
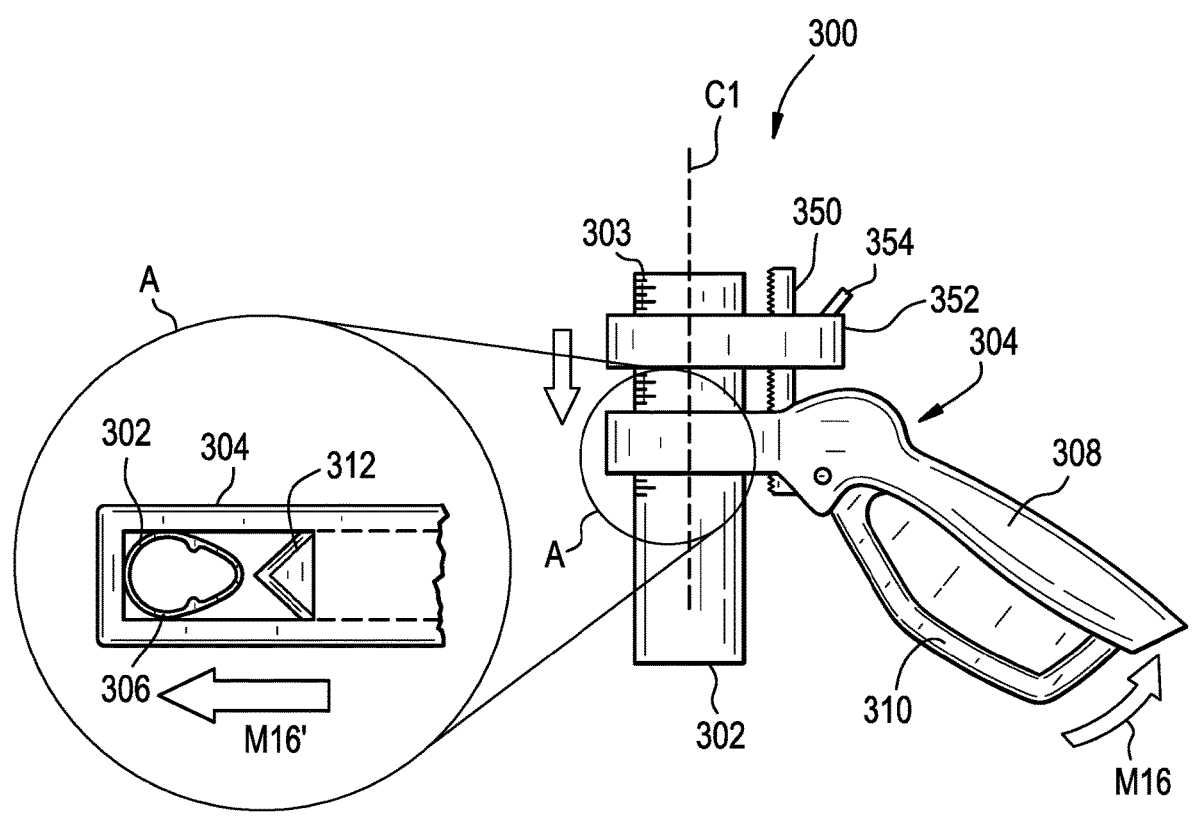

FIG. 16 illustrates another embodiment of an access port cutter 300 for cutting an access port 302. The access port cutter 300 can have a base 304 with an opening 306 and a grip 308. The opening 306 can receive the access port 302 therein. In some embodiments, the access port 302 can have visual markings 303 along an outer surface that can aid a user in placing the access port 302 within the access port cutter 300. A handle 310 can move relative to the base 308 in a direction M16 such that a blade 312 can translate linearly along a cut path M16' across the opening 306. The access port cutter 300 can include an adjustable guide 350 and a clamp 352 that can help align the base 304 and, accordingly, the blade 312, with respect to the access port 302. The guide 350 can be a rigid post that can extend proximally from the base 304 of the access port cutter 300 parallel to a longitudinal axis C1 of the opening 306. As such, the guide 350 can extend parallel to a longitudinal axis of the access port 302 when the access port is received within the opening 306. The clamp 352 can have an opening (not shown) for receiving the access port 302 and can translate longitudinally along the guide 350. A guide lock 354 can be moved between a first position in which the clamp 352 can move relative to the guide 350 and a second position in which movement is restricted therebetween. The clamp 352 can be moved longitudinally along the guide 350 to a position that can stabilize the access port 302 relative to the access port cutter 300.

Figure 17:
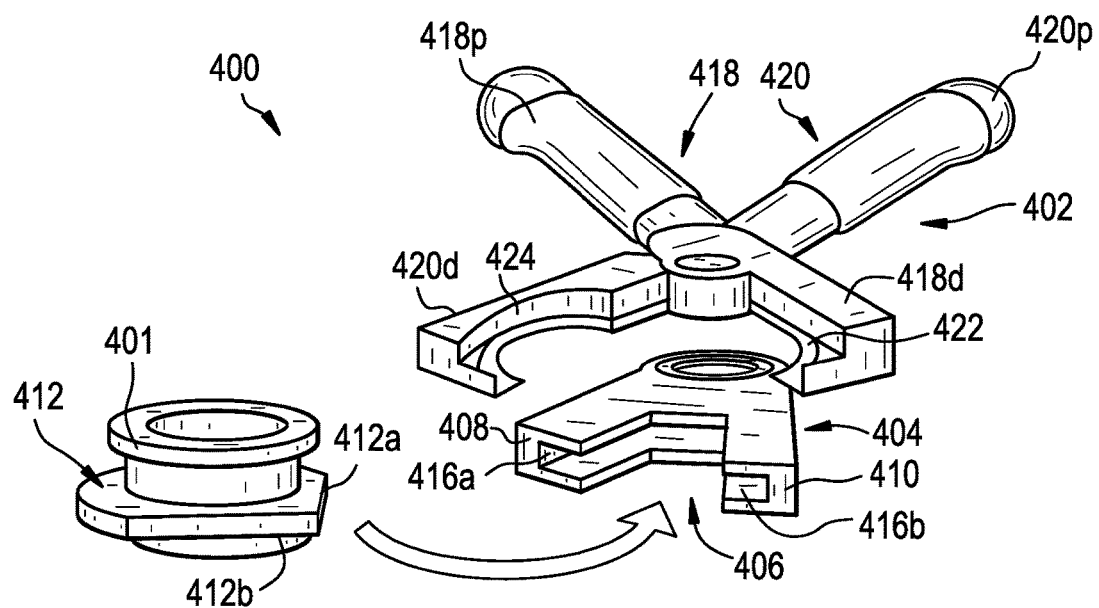
Figure 18:
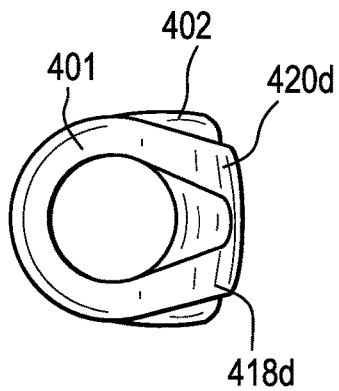
Figure 19:
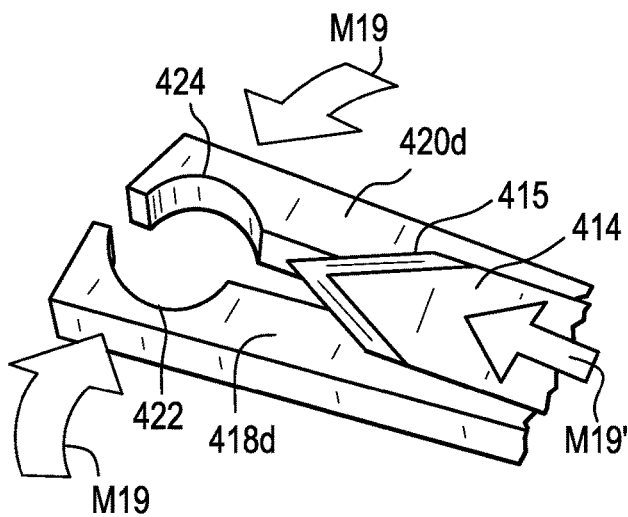

FIGS. 17-19 illustrate an embodiment of an access port cutter 400 with an integrated clamping mechanism 402 that can couple the access port cutter to an access port. FIG. 17 shows the access port cutter 400, which can include a base 404 with an opening 406 extending between a first arm 408 and a second arm 410 of the base. An access port holder 412 can be inserted into the opening 406 through a first end of the base and can receive an access port 401 therethrough. More particularly, a groove 416*a*, 416*b* can extend along the first and second arm 408, 410 and can receive a first edge 412*a* and a second edge 412*b* of the holder 412, respectively. The holder 412 can assist in orienting the base 404 relative to the access port 401 such that a blade 414 (FIG. 19) can extend from the base and traverse the opening 406 to cut through the access port. The base 404 can be integrated or otherwise securely attached to the clamping mechanism 402 at a second end of the base. The clamping mechanism 402 can include a first lever arm 418 and a second lever arm 420 that can be arranged in a scissor-like manner. A proximal portion 418p, 420p of the lever arms 418, 420 can be brought towards one another to move distal portion 418d, 420d of the lever arms, which can each have a recessed portion 422, 424, towards one another such that the recessed portions can clamp or securely hold the access port 401 therebetween. The arms 418, 420 can extend such that when the distal portions 418d, 429d are moved towards one another, the recessed portions 422, 424 can substantially align with the access port holder 412 received within the opening 406 of the base 402 (FIG. 18). FIG. 19 schematically illustrates an embodiment of mechanics of the access port cutter 400 with the access port 401 inserted into the access port holder 410. The distal portions 418d, 420d of the lever arms 418, 420 can be brought towards one another, i.e., in the direction M19, such that the recessed portion 422, 424 can secure the access port 401 therebetween. The blade 414 can then be driven linearly along a portion of the base 404, i.e., in the direction M19', and a cutting edge 415 of the blade 414 can traverse the opening of the access port holder 412 to cut through the access port 402.

Figure 20:
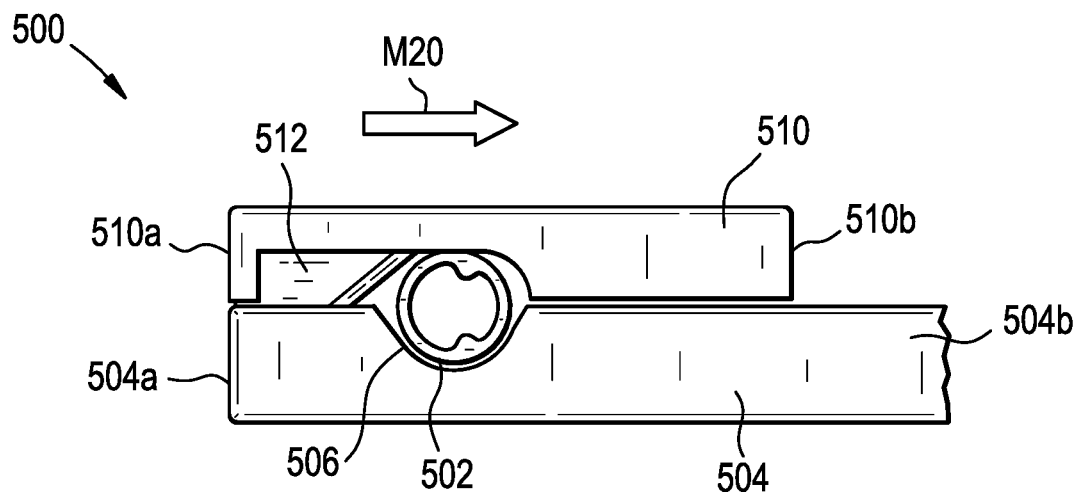
Figure 21:
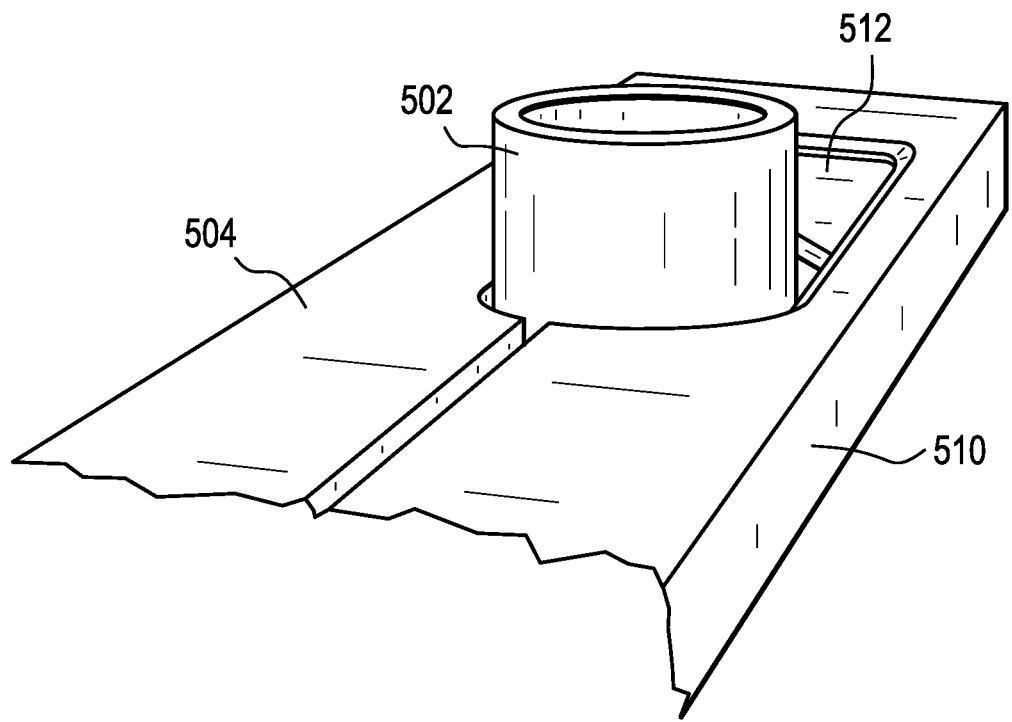

FIGS. 20 and 21 illustrate another embodiment of an access port cutter 500 for cutting an access port 502. The access port cutter 500 can include a base 504 with a proximal end 504a and a distal end 504b. A blade 512 can glide or translate across an opening 506 that can be formed between the base 504 and a handle 510. More particularly, the opening 506 can be sized and shaped to receive the access port 502 therein and can be formed between a recessed edge of the base 504 and a counterpart edge of the handle 510. The handle 510 can have a proximal portion 510a that can extend beyond the opening 506 and can form a lever arm relative to a distal portion 510b of the handle. The blade 512 can extend distally from the proximal portion 510a of the handle 510 such that a cutting edge of the blade can face towards the opening 506. A user can translate the handle 510 in the direction M20, i.e., distally relative to the base 504, such that the blade 512 can traverse the opening 506 and can cut through the access port 502 received therein. The access port 502 can be rotated within the opening 506, if needed, such that the blade can cut across an entire perimeter of the access port.

Figure 22:
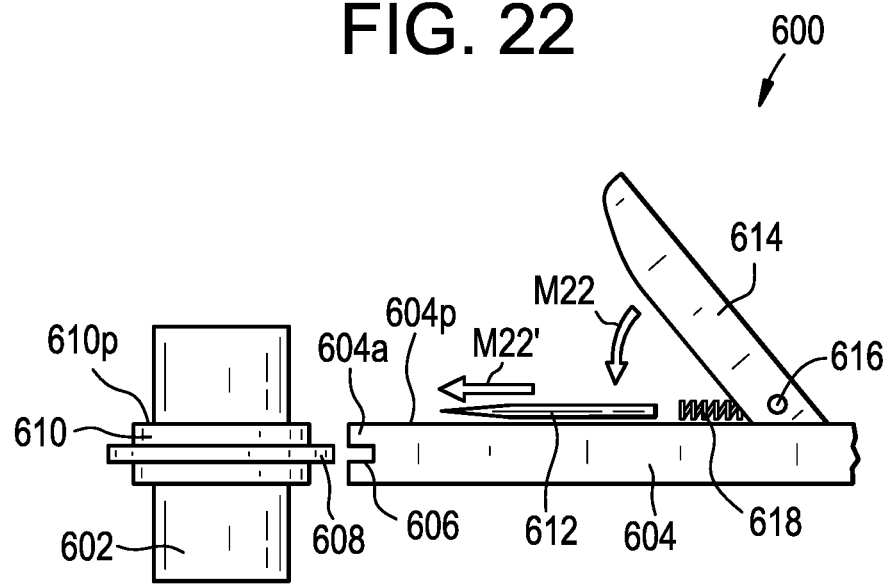

FIG. 22 illustrates another embodiment of an access port cutter 600 that can cut an access port 602 to a desired length. The access port cutter 600 can have a base 604 with an attachment feature 606 at a first end 604a thereof. The attachment feature 606 can engage with a counterpart attachment feature 608 of an access port ring 610. The access port ring 610 can have a lumen extending therethrough configured to receive the access port 602. The access port ring 610 can be placed along the access port 602 such that a desired length of the access port can extend distally from a proximal-facing surface 610p of the access port ring 610. In some embodiments, the engagement feature 606 of the base 604 can be a groove and the counterpart engagement feature 608 of the access port ring 610 can be a lip or protrusion. The engagement feature 606 of the base 604 can couple with the engagement feature 608 of the access port ring 610 such that a proximal-facing surface 604p of the base 604 can align with the proximal-facing surface 610p of the ring 610.

The access port cutter 600 can also include a blade 612 that can translate across at least a portion of the proximal-facing surface 604p of the base 604. A handle 614 can be pivotably coupled to the base 604 about a pivot point 616. In some embodiments, the blade 612 can be spring-loaded with a spring 618. The handle 614 can be pivoted relative to the base 604 such that the spring 618 can exert a spring force on the blade 610 and can drive the blade towards the base's first end 604a. The blade 612 can be spring-loaded such that the handle 614 can be moved to a final position in the direction M22 and the blade can translate in the direction M22' to traverse the opening of the access port ring 610 along the proximal-facing surface 610p of the access port ring.

Figure 23:
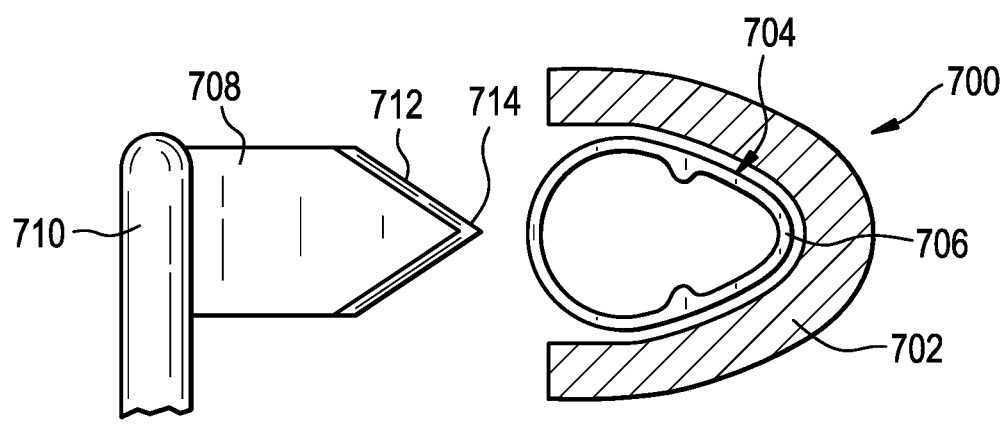

FIG. 23 shows an access port cutter 700 that can include a base 702 with an opening 704 that can receive an access port 706 therein. In some embodiments, the opening 704 can be generally "C" or "U" shaped such that the access port 706 can be laterally inserted into the opening. A shape of the opening 704 can permit non-cylindrical access ports, such as the access port 706 illustrated having an oval perimeter, to be received therein. A blade 708 can extend from a handle 710 with a cutting edge 712 of the blade facing towards the opening 704 of the base 702. The handle 710 can be moved towards the base 702 such that a sharp tip 714 of the blade 708 can contact and pierce the access port 706 received within the opening 704. The cutting edge 712 of the blade 708 can traverse the opening 704 and can cut across the access port 706. Piercing the access port 706 with the sharp tip 714 of the blade 708 can prevent or reduce deformation of the access port while the cutting edge 712 of the blade cuts across the access port.

Figure 24:
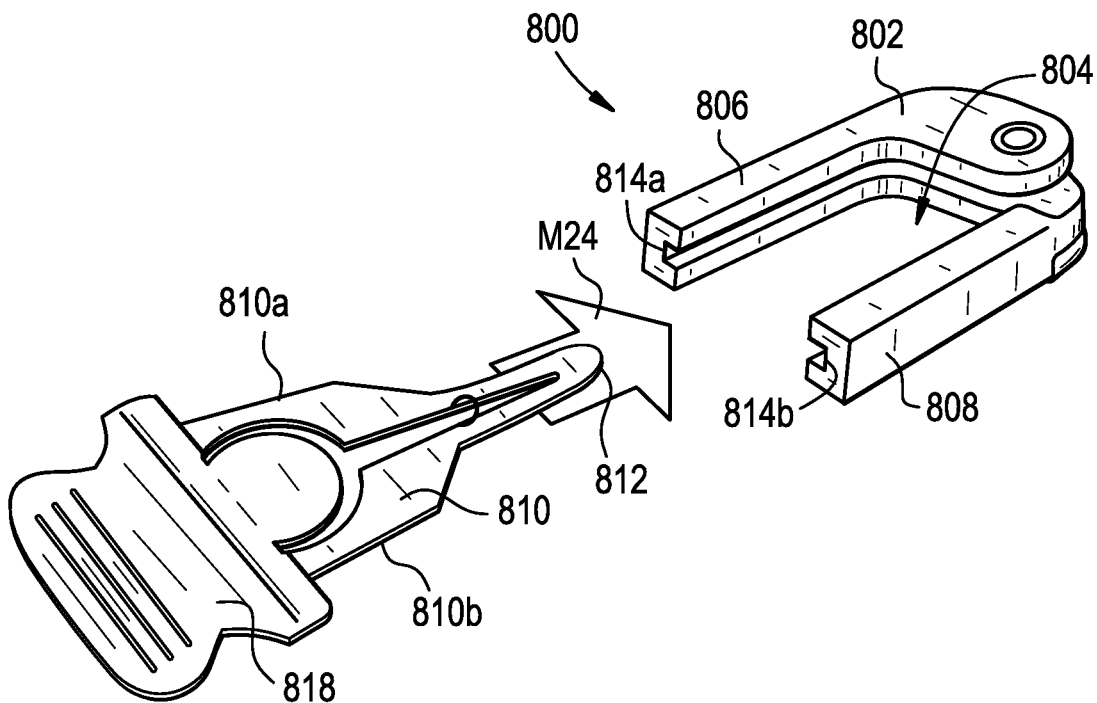

FIG. 24 illustrates another embodiment of an access port cutter 800. The access port cutter 800 can include a base 802 with an opening 804 formed between a first arm 806 and a second arm 808. The opening 804 can be sized such that an access port (see FIG. 1) can be received therein, with a longitudinal axis of the access port extending perpendicular to a longitudinal axis of the first and second arms 806, 808. A blade 810 can have a cutting edge 812 and can be slidably received within the base 802 such that the blade can traverse the opening 804 and can cut through the access port received therein. More particularly, a groove 814a, 814b can be formed within the first arm 806 and the second arm 808 along substantially an entire length of each arm. A first edge 810a of the blade 810 and a second edge 810b of the blade can be received within the groove 814a, 814b of the first and second arms 806, 808 respectively. An end of the blade 816 opposite the cutting edge 812 can be secured to a loading tool 818 that can be gripped by a user to insert the blade into the opening and translate the blade within the opening in the direction M24. In some embodiments, the base 802 can be designed for reuse while the blade 810 and the loading tool 818 can be disposable.

Figure 25:
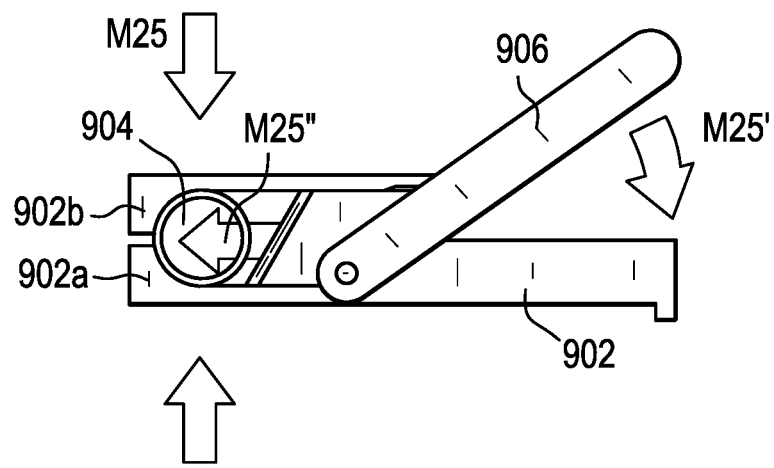

FIG. 25 illustrates another embodiment of an access port cutter 900. The access port cutter 900 can have a base 902 with a first arm 902a and a second arm 902b forming an opening 904 therebetween. The first and second arms 902a, 902b can separate from one another which can enlarge the opening 904 and can aid in inserting an access port (see FIG. 1) into the opening. The arms 902a, 902b can then move back towards one another in the direction M25 and can secure the access port within the opening 904 relative to the base 902. A handle 906 can pivot relative to the base 902. The handle 906 can be moved towards the base 902 in the direction M25', which can drive a blade 908 linearly along a cutting path M25". The blade 908 can translate along at least a portion of the base 902 such that the blade can traverse the opening 904 and cut across the access port received therein.

Figure 26:
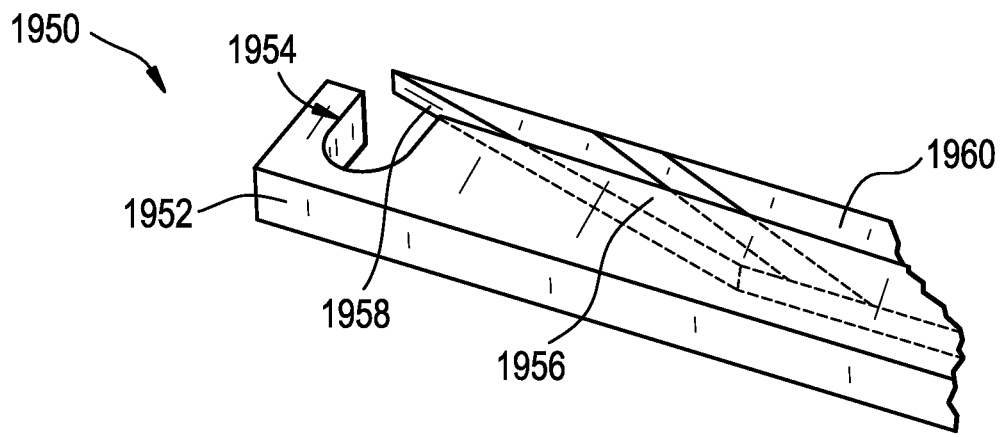

FIG. 26 shows another embodiment of an access port cutter 1950 that can have a base 1952 with an opening 1954.

In some embodiments, the opening 1954 can be substantially "C" or "U" shaped such that an access port (FIG. 1) can be inserted laterally into the opening. A blade 1956 with a cutting edge 1958 can extend from a handle 1960. The handle 1960 can be moved relative to the base 1952 such that the cutting edge 1958 of the blade 1956 can traverse the opening 1954 and can cut across an access port received therein.

Figure 27:
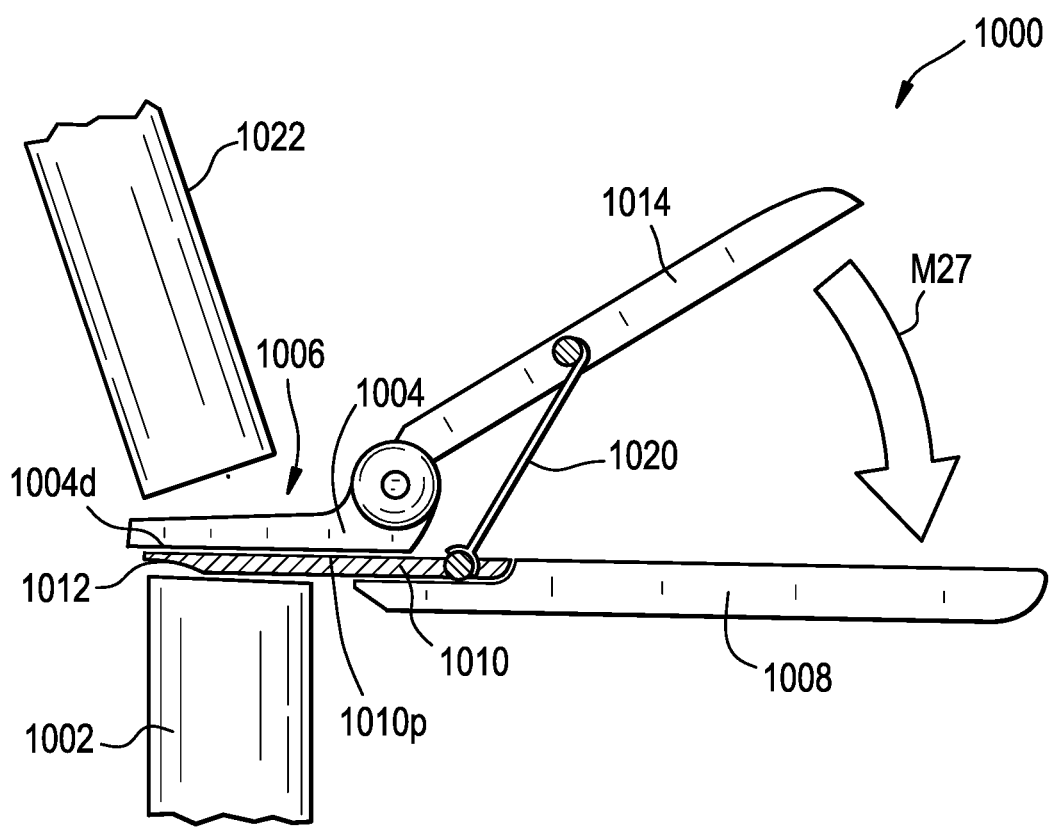

FIG. 27 illustrates another embodiment of an access port cutter 1000 with a linkage mechanism that can be actuated to drive a blade linearly across an opening to cut an access port 1002. More particularly, the access port cutter 1000 can have a base 1004 with an opening 1006 extending therethrough. A grip portion 1008 can extend laterally from a distal surface 1004d of the base 1004. A blade 1010 can slidably extend from the grip 1008 with a cutting edge 1012 of the blade 1010 facing towards the opening 1006. A proximal surface 1010p of the blade 1010 can be flush with the distal surface 1004d of the base 1004. A handle 1014 can be pivotably connected to the base 1004 such that the handle 1014 can be moved towards the grip 1008 in the direction M27. A linkage 1020 can extend between the handle 1014 and the blade 1010 such that movement of the handle 1014 towards the grip 1008 can cause the blade 1010 to linearly translate in the direction of the opening 1006. The handle 1014 can be closed, i.e., moved towards the grip 1008, which can cause the cutting edge 1012 to traverse the opening 1006 and cut through the access port 1002 received therein. After the cut, a waste portion 1022 of the access port 1002 can be removed proximally from the base 1004.

Figure 28:
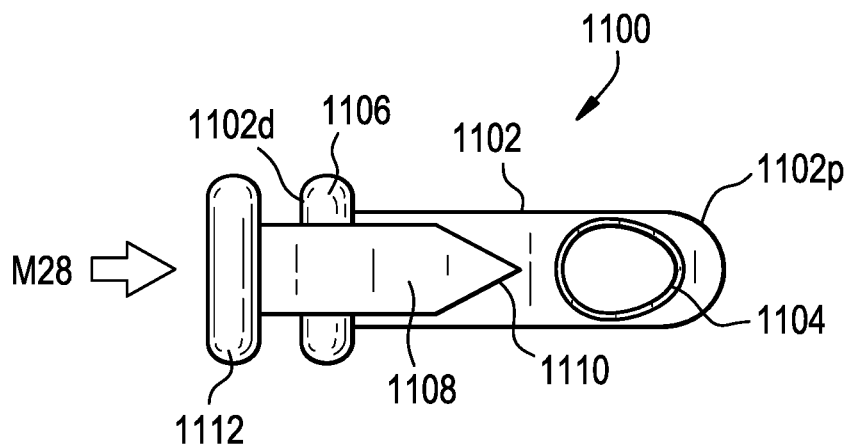

FIGS. 28-31 illustrate various embodiments of access port cutters of the present disclosure that can be operated by a user with a single hand to cut an access port to a desired length at a point of use. FIG. 28 shows an access port cutter 1100 that can include a base 1102 with an opening 1104 located towards a proximal end 1102p thereof. The base 1102 can have a grip portion 1106 at a distal end 1102d such that a user can hold the base with an access port (see FIG. 1) received within the opening 1104. A blade 1108 can have a cutting edge 1110 and a handle 1112 opposite the cutting edge. The blade 1108 can be positioned along the base 1102 with the cutting edge 1110 facing towards, but remote from, the opening 1104. At least a portion of the blade 1110 and the handle 1112 can extend distally from the distal end 1102d of the base. A user can grip the handle 1112 and can move the handle towards the base 1102 in the direction M28 such that the blade 1108 can translate linearly along the base towards the proximal end 1102p of the base. The cutting edge 1110 of the blade 1108 can traverse the opening 1104 and can cut across the access port received therein. The handle 1112 can be brought into alignment with the grip 1106 to move the cutting edge 1110 fully across the opening 1104. In some embodiments, the handle 1112 can be shaped as a palm rest for a user's hand and the grip 1106 can extend generally perpendicular to the base 1102 such that a user can place at least one finger on either end of the grip.

Figure 29:
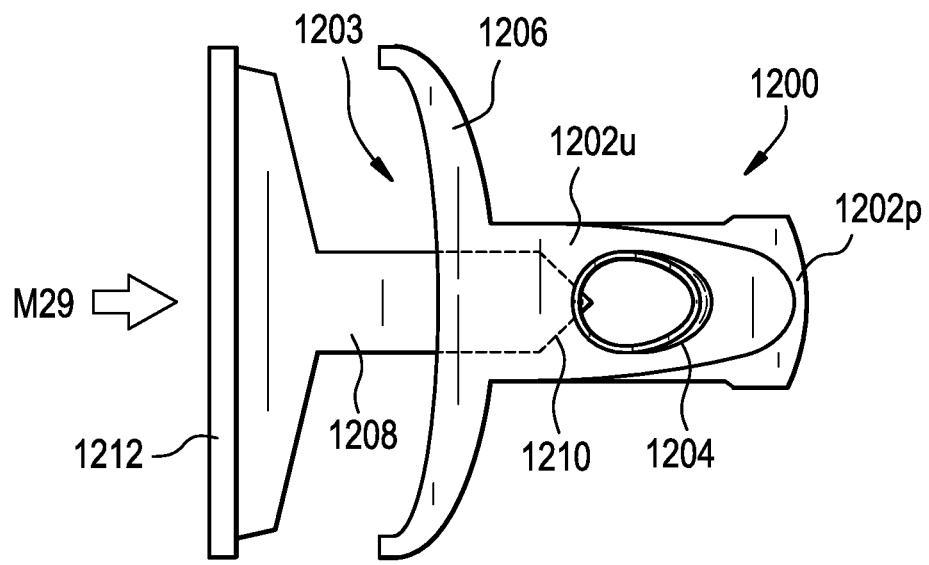

FIG. 29 shows an access port cutter 1200 that can be similar to the access port cutter 1100 of FIG. 28 except that a base 1202 of the access port cutter 1200 can have an upper planar surface 1202u and a lower planar surface (not visible) with a slot 1203 extending therebetween. Like-numbered features of the access port cutter 1200 of FIG. 29 to that of the access port cutter 1100 of FIG. 28 can be identical or similar except as discussed herein. Accordingly, description of such features is omitted for the sake of brevity. A blade 1208 can be inserted into the slot 1203 of the base 1202 such that a cutting edge 1210 can face towards an opening 1204 and can traverse the opening 1204 with a forward force M29 exerted on the blade 1208.

Figure 30:
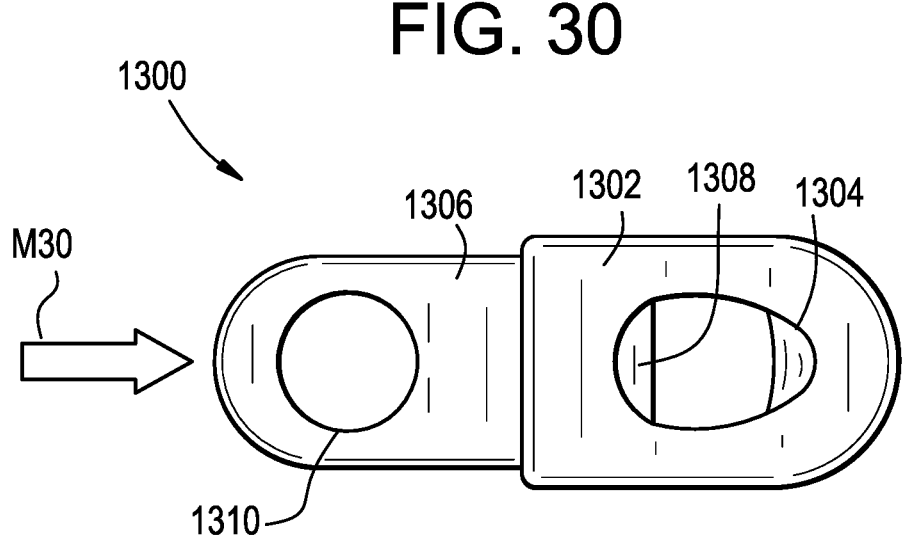

FIG. 30 shows another embodiment of an access port cutter 1300. The access port cutter 1300 can include a base 1302 with an opening 1304 that can receive an access port (FIG. 1) therein. A handle 1306 can be slidably received within the base 1302 such that a cutting edge 1308 of the handle can traverse the opening 1304 and cut across the access port. The handle 1306 can have grip opening 1310 located towards an end of the handle 1306 opposite the cutting edge 1308. In some embodiments, the opening 1310 can be a thumb or finger grip. The handle 1310 can be moved towards the opening 1304 of the base 1302 in a direction M30 such that the cutting edge 1308 traverses the opening 1304.

Figure 31:
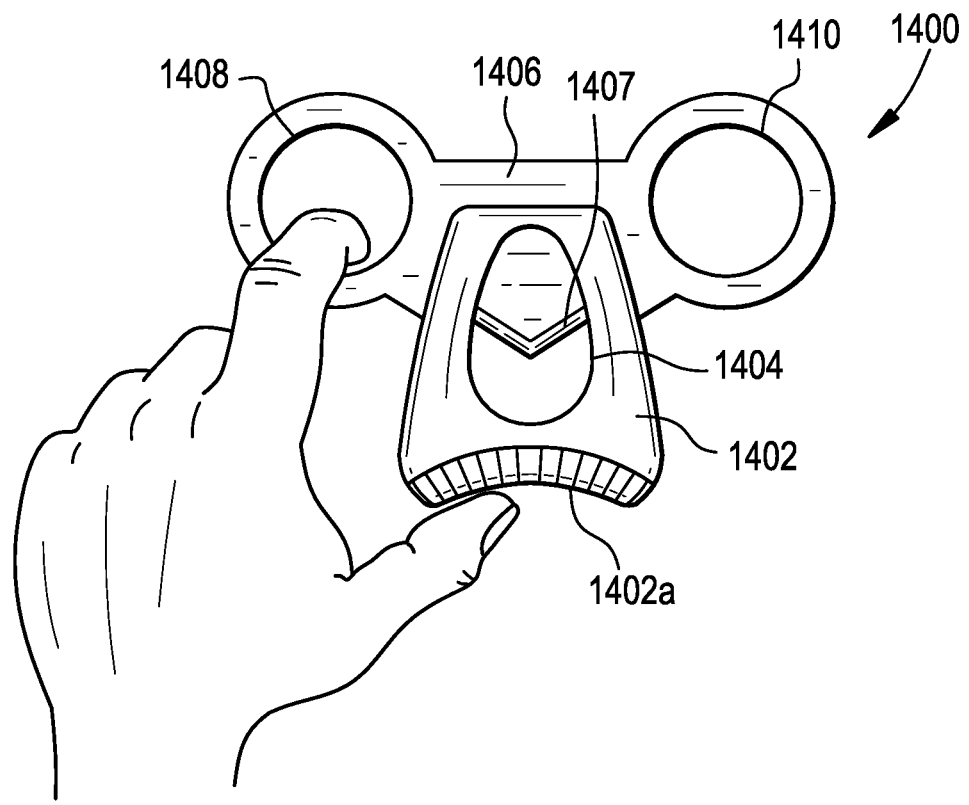

FIG. 31 illustrates another embodiment of an access port cutter 1400. In some embodiments, the access port cutter 1400 can be small and disposable. The access port cutter 1400 can include a base 1402 with an opening 1404 to receive an access port (FIG. 1) therein. The base can have a first end 1402a that can be shaped to conform to a user's thumb or hand. A handle 1406 can be slidably received within the base 1402 such that a cutting edge 1407 of the handle can traverse the opening 1404. In some embodiments, the handle 1406 can be inserted into the base 1402 from a side opposite the first end 1402a and the handle can slide along a portion of the base such that the cutting edge 1407 can move across the opening 1404 towards the first end 1402a. The handle 1406 can have a first grip opening 1408 and a second grip opening 1410 that can be accessible to a user when the handle is received within the base 1402. In some embodiments, the first and second grip openings 1408, 1410 can extend through opposite ends of a lateral portion of the handle 1406 such that one of the grip openings 1408, 1410 can be placed on either side of the base 1402. A user can place their thumb against the first side 1402a of the base and a finger through one of the first or second grip openings 1408, 1410 of the handle 1406 and can move the handle 1406 relative to the base 1402 such that the cutting edge 1407 traverses the opening 1404.

Figure 32:
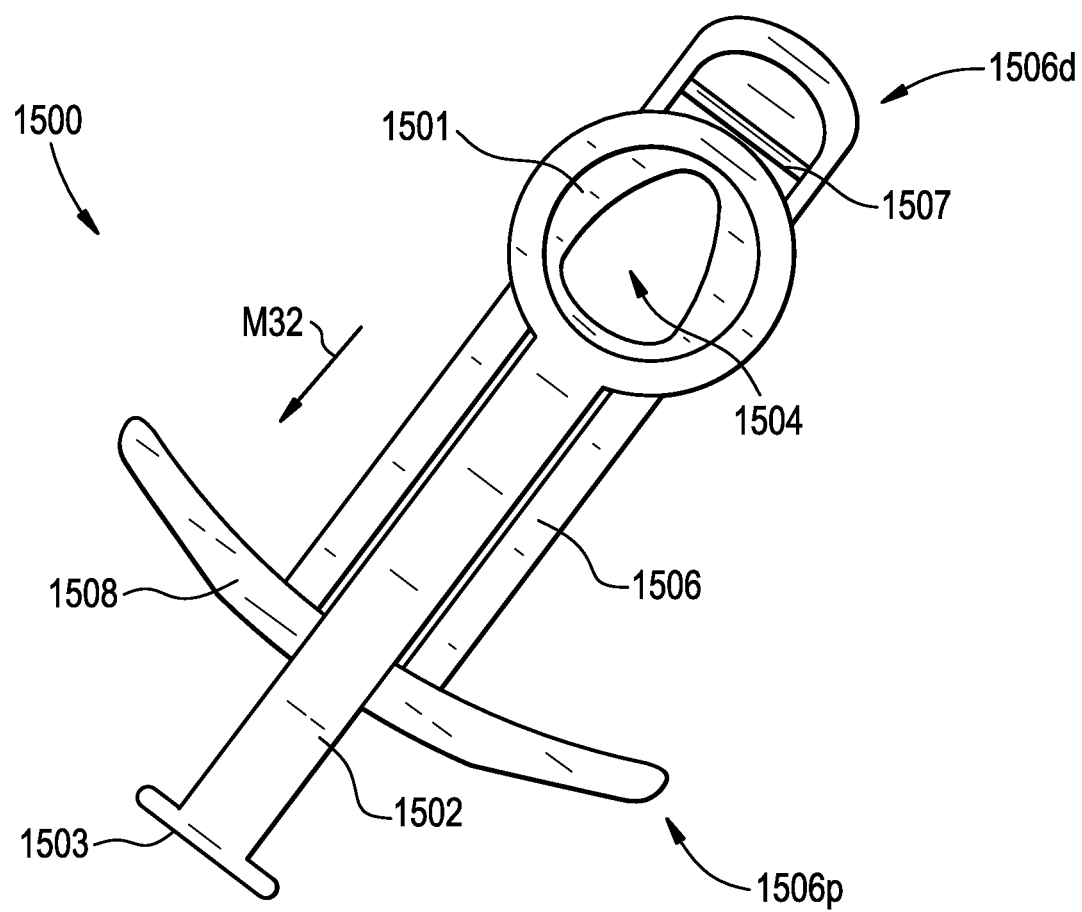

FIG. 32 shows another embodiment of an access port cutter 1500 that can be similar to the access port cutter 1400 of FIG. 31. Except as described herein, like-numbered features of the access port cutter 1500 can be similar or identical to those of the access port cutter 1400 of FIG. 31. Accordingly, description of such features is omitted for the sake of brevity. The access port cutter 1500 can include a base 1502 with an opening 1504 to receive an access port 1501 therein. The base 1502 can have a palm rest 1503 at a proximal end opposite the opening 1504, which can facilitate a stable hold of the base 1502 in a user's hand. A handle 1506 can have a cutting edge 1507 located at a distal end 1506d thereof and a grip 1508 at a proximal end 1506p. The grip 1508 can extend laterally relative to a longitudinal axis of handle 1506. In some embodiments, the grip 1508 can be designed such that a user can hold the grip with one or more fingers on either side of the handle 1506 while the palm rest 1503 of the base 1502 is within the user's hand. The handle 1506 can be slidably received within the base 1502 such that a user can pull the handle proximally, i.e., in a direction M32, relative to the base 1502, causing the cutting edge 1507 of the handle to move proximally and traverse the opening 1504.

Figure 33:
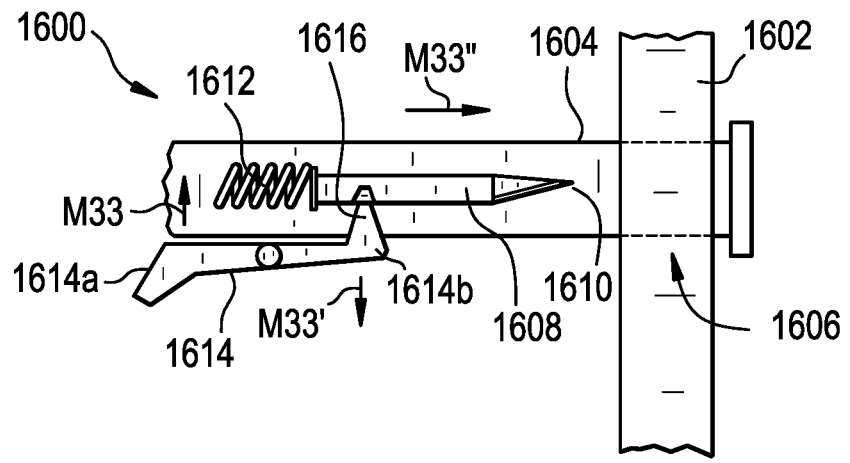

FIG. 33 shows a side view of another embodiment of an access port cutter 1600 that can have a spring-loaded blade to cut across an access port 1602. The access port cutter 1600 can include a base 1604 with an opening 1606 that can receive the access port 1602 therein. A blade 1608 can be slidably received within the base 1604 with a cutting edge 1610 of the blade facing towards the opening 1606. The blade 1608 can be spring-loaded with a spring 1612. A lever arm 1614 can have an extension 1616 on a first end 1614a of the arm. The extension 1616 can engage with a counterpart recess or opening (not shown) in the blade 1608 such that the spring 1612 can be held in a compressed position and the blade 1608 can be prevented from translating forward towards the opening 1606. An upward force M33 towards the base 1604 can be applied to a second end 1614b of the lever arm such that the extension 1616 can disengage and move away from the blade 1608, i.e., in the direction M33'. The spring 1612 can be released and extend distally to translate the blade 1608 towards the opening 1606, i.e., in the direction M33", such that the cutting edge 1610 of the blade can traverse the opening and cut across the access port 1602 received therein.

Figure 34:
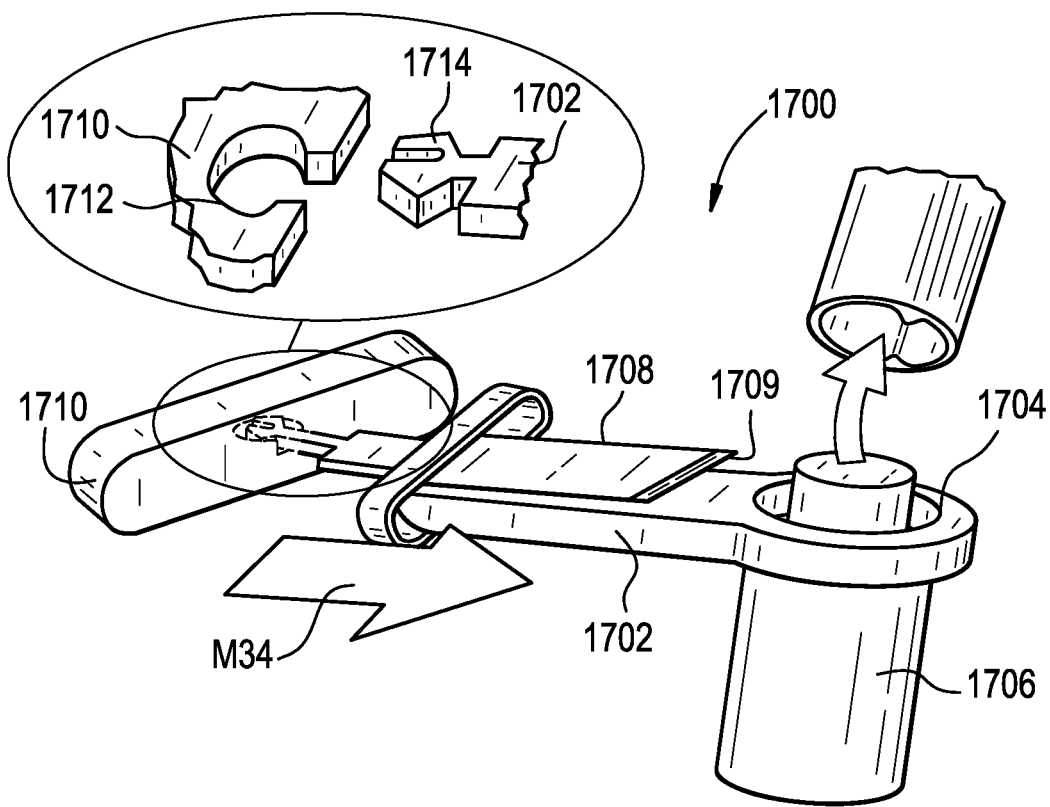

FIG. 34 shows another embodiment of an access port cutter 1700 that can include a base 1702 with an opening 1704 that can receive an access port 1706 therein. A blade 1708 can extend from a handle 1710 with a cutting edge 1709 of the blade facing towards the opening 1704. The handle 1710 can be moved in the direction M34 towards the opening 1704 such that the cutting edge 1709 of the blade 1708 can traverse the opening and cut across the access port 1706. The handle 1710 can have a locking feature, such as a recess 1712, that can engage with a counterpart feature of the base 1702, such as an extension 1714, to lock the handle to the base and restrict movement therebetween after a cutting action is completed. The counterpart locking features of the handle 1710 and the base 17002 can engage with one another when the handle is in a position that corresponds to a point at which the cutting edge of the blade 1708 has traversed across an entire surface area of the opening 1704. This locking can prevent a user from retracting the blade inadvertently, which could result in injury or dropping cut debris down the cut access port 1706 toward the surgical site.

Figure 35:
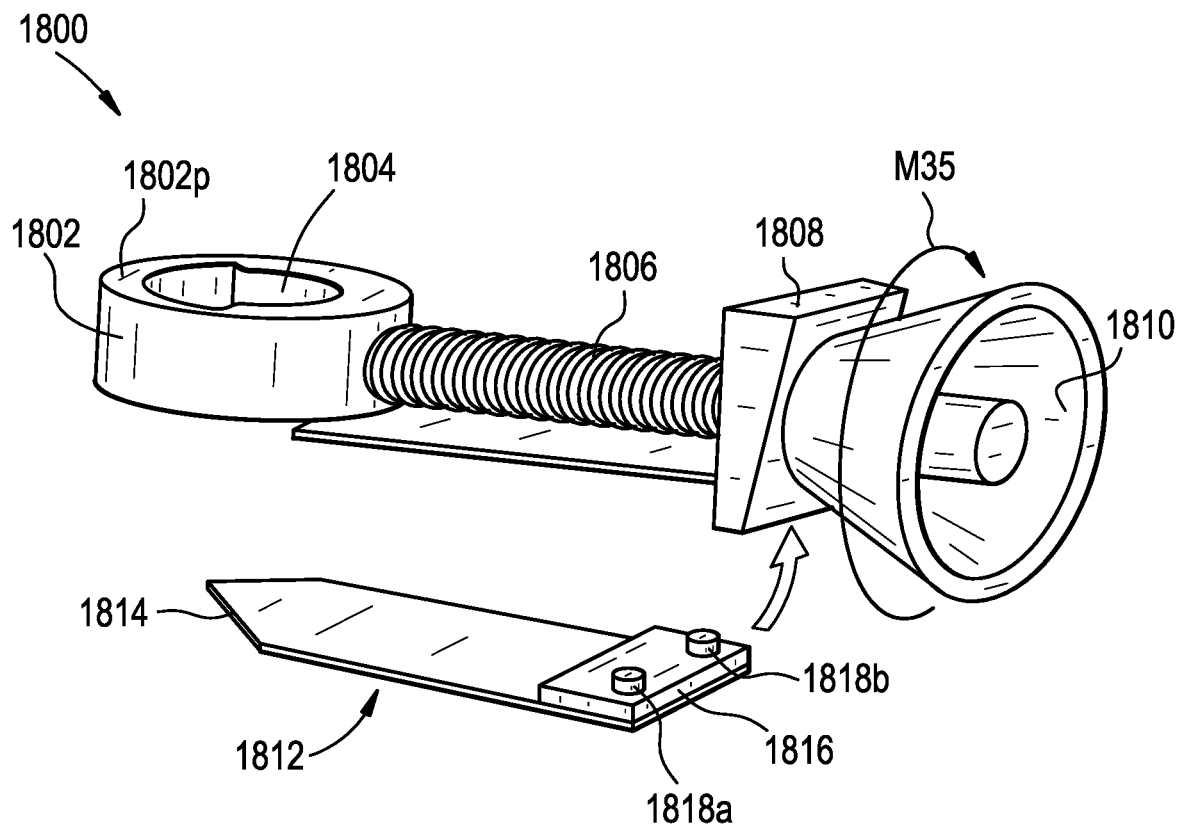
Figure 36:
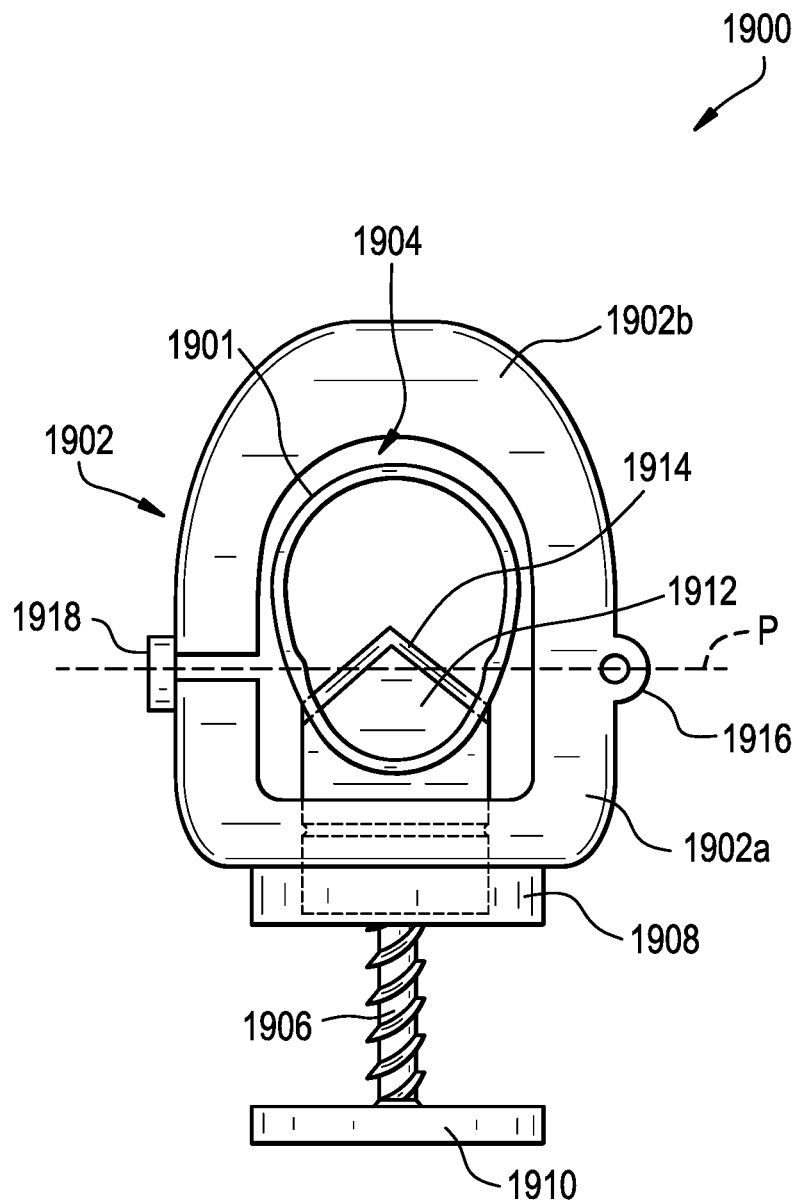

FIGS. 35 and 36 show embodiments of access port cutters of the present disclosure that can include a screw-style handle that can drive a screw to linearly translate a blade across an opening of the access port cutter. FIG. 35 shows an access port cutter 1800 that can include a base 1802 with an opening 1304. A threaded shaft 1806 can extend from the base 1802 through a block 1808 to a handle 1810. The handle 1810 can be rotated in a first direction, e.g., clockwise as shown by arrow M35, which can cause the block 1808 to translate along the shaft 1806 towards the base 1802. A blade 1812 can have a cutting edge 1814 at a first end thereof and an attachment component 1816 at a second end opposite the cutting edge. The attachment component 1816 can include one or more attachment features, e.g., posts 1818a, 1818b, that can engage with counterpart attachment features of the block 1808, e.g., recesses (not shown), to securely attach the blade 1812 to the block 1808 with the cutting edge 1814 facing towards the opening 1804 of the base 1802. Accordingly, the blade 1812 can advance with the block 1808 as the block moves along the shaft 1808 towards the base 1802. The block 1808 can be advanced towards the base 1802 until the cutting edge 1814 of the blade 1812 can traverse the opening 1804 and can cut across an access port received therein. In some embodiments, the blade 1812 can be attached to the block 1808 such that the blade 1812 can translate across a proximal-facing surface 1802p or a distal-facing surface (not shown) of the base 1802.

FIG. 36 illustrates another embodiment of an access port cutter 1900 that can have a base 1902 with an opening 1904 extending therethrough to receive an access port 1901. The base 1902 can have a first portion 1902a and a second portion 1902b that can be pivotably connected to one another. Similar to the access port cutter 1800 described above, a threaded shaft 1906 can extend from the first portion 1902a of the base through a block 1908 to a handle 1910. The handle 1910 can be rotated which can translate the block 1908 and, accordingly, a blade 1912 that can be secured to the block towards the base 1902 such that a cutting edge 1914 of the blade can traverse the opening and cut across the access port 1901. The first portion 1902a of the base can be connected to the second portion of the base 1902b with a hinge 1916 such that the first portion can pivot about an axis P relative to the second portion of the base. Put another way, an angle of the first portion 1902a relative to the second portion 1902b can be adjusted in a direction into or out of the page of FIG. 36 about the hinge 1916. As the threaded shaft 1908 extends from the first portion 1902a of the base, adjusting the angle of the first portion can simultaneously adjust an angle at which the blade 1912 can traverse the opening 1904 and cut through the access port 1901. The hinge 1916 can be locked into place with a lock 1918 such that relative movement between the first portion 1902a and the second portion 1902b can be restricted. In this manner, the angle at which the access port cutter 1900 can cut the access port 1901 can be varied based on particular needs of a patient and/or surgical procedure. This can allow the access port to be cut with a beveled or angled end to better fit in a surgical site around particular patient anatomy.

Figure 37:
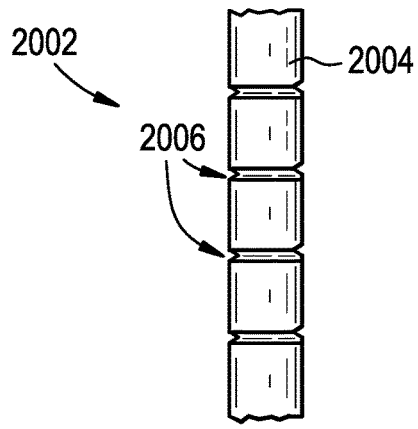
Figure 38:
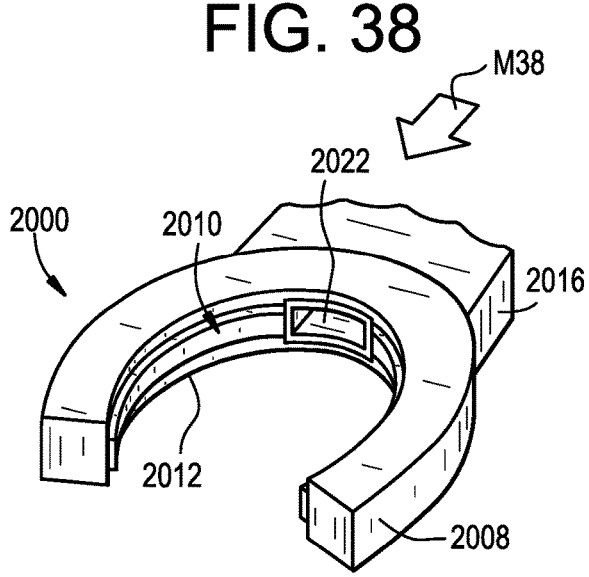
Figure 39:
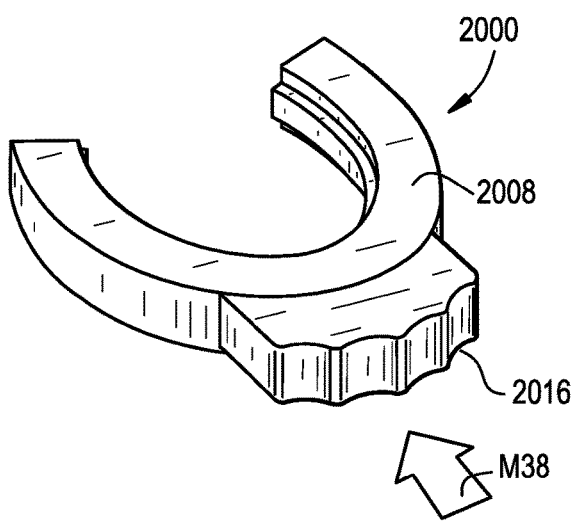
Figure 40:
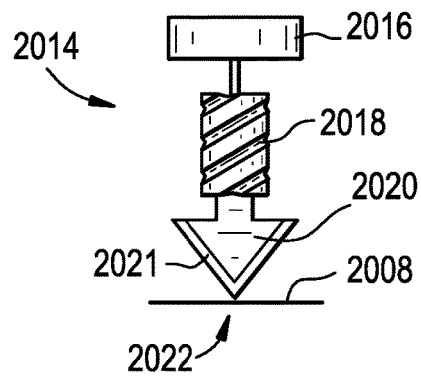

FIGS. 37-40 illustrate another embodiment of an access port cutter 2000. FIG. 37 illustrates an embodiment of an access port 2002 that can be used with the access port cutter 2000. The access port 2002 can have a tubular body 2004 with one or more weak points 2006 along a length of the body. In some embodiments, the weak points 2006 can have a reduced diameter and/or reduced wall thickness than the remainder of the tubular body 2004. FIGS. 38 and 39 show perspective views of the access port cutter 2000 that can have a base 2008 with an access port opening 2010. The opening 2010 can be configured to receive the access port 2002 therein and, more particularly, one of the weak point(s) 2006 of the port. For example, in some embodiments, a lip 2012 can have a counterpart geometry to the weak point(s) 2006 of the access port 2002 and can protrude into the opening 2010 such that the lip can align with the weak point of the access port. The access port cutter 2000 can include a spring-button mechanism 2014 (FIG. 40) that can extend through the base 2008. A button 2016 of the mechanism 2014 can be depressed towards the base 2008, i.e., in the direction M38, such that a spring 2018 can exert a spring force on a blade 2020. The spring 2018 can drive the blade 2020 through an opening 2022 in the base 2008 and into the access port opening 2010 such that a cutting edge 2021 of the blade can traverse the access port opening and can cut across the access port 2004 received therein.

Figure 41A:
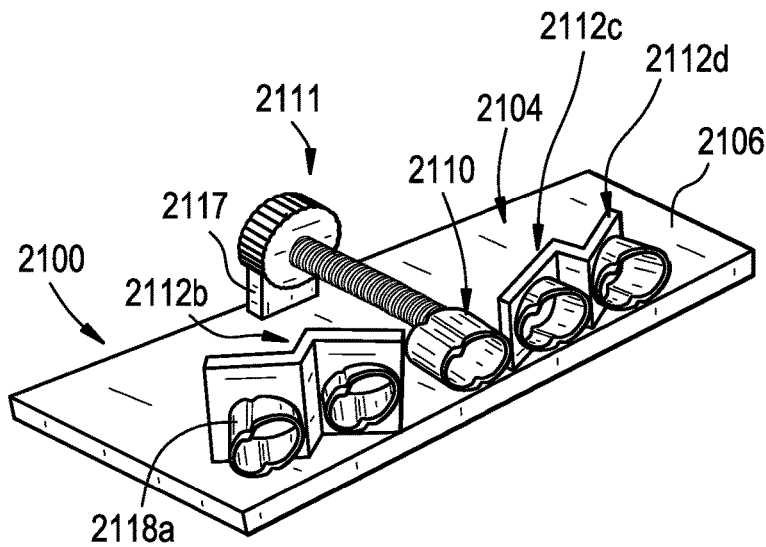
FIG. 41A is a perspective view of another embodiment of an access port cutter of the present disclosure.
Figure 41B:
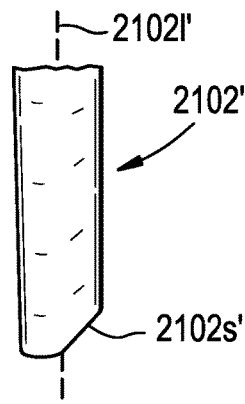
FIG. 41B illustrates one embodiment of an access port that can have a beveled end cut by the access port cutter of FIG. 41A.
Figure 42:
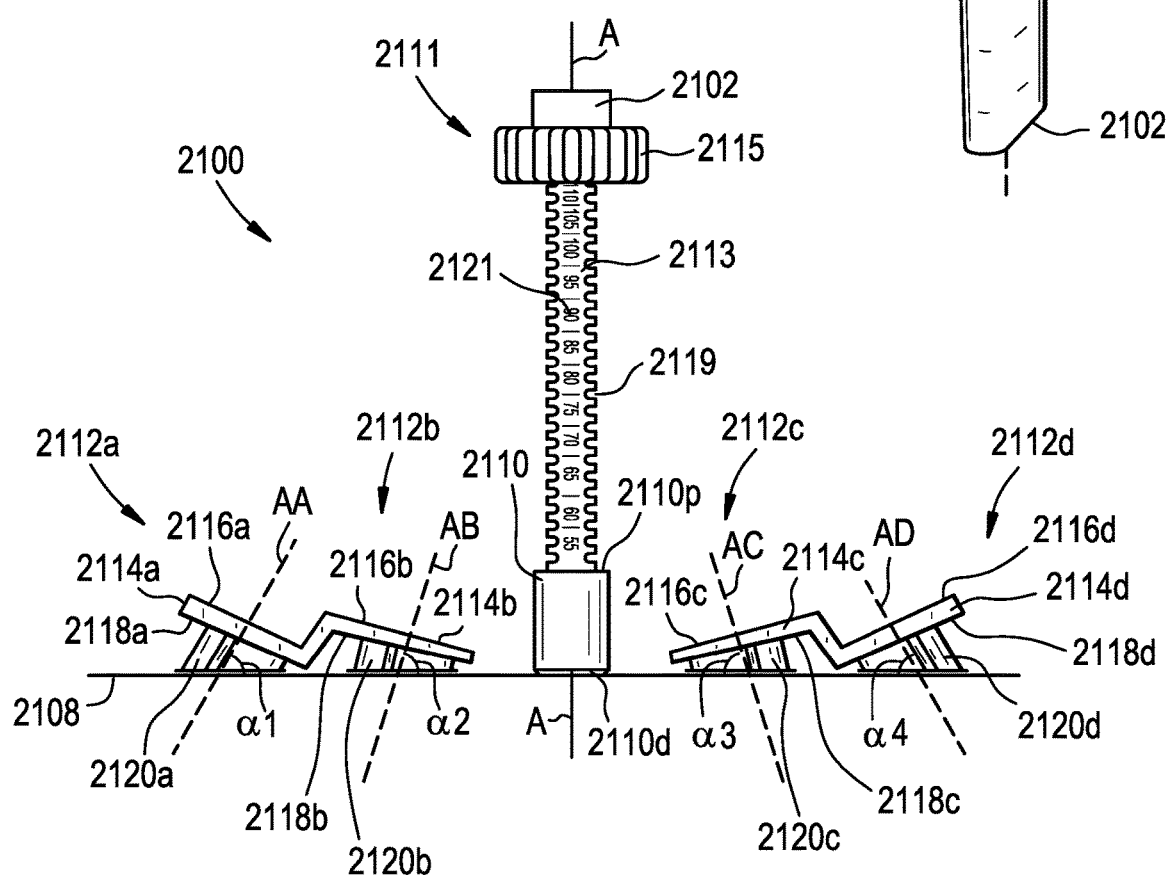
FIG. 42 is a top view of the access port cutter of FIG. 41A.

FIGS. 41A, 41B, and 42 illustrate another embodiment of an access port cutter 2100 that can cut an access port 2102 at a plurality of angles. The access port cutter 2100 can cut the access port 2102 with a straight cut, i.e., such that a cut surface of the access port can extend perpendicular to a longitudinal axis of the access port, or with a bevel cut, i.e., a cut surface 2102s' of the access port 2102' can extend at an oblique angle relative to a longitudinal axis 21021' of the access port as shown in FIG. 41B. The access port 2102' with the beveled surface 2102s' can be cut at a particular oblique angle to account for variations in patient anatomy at the surgical site or along a surgical approach. For example, the beveled surface 2102' can be cut at an angle to better fit bony anatomy of a spinal surgical site.

The access port cutter 2100 can be placed or mounted on a table or hard surface located within an operating room or a surgical field. Mounting the access port cutter 2100 can enable use of a larger lever arm for cutting through an access port, which can increase a thickness and/or stiffness of an access port that can be cut. FIG. 41A shows a perspective view of the access port cutter 2100 and FIG. 42 shows a top-down view of the access port cutter of FIG. 41A. The access port cutter 2100 can include a base 2104 that can have a planar surface 2106 and a cutting surface 2108. The cutting surface 2108 can be perpendicular to the planar surface 2106 such that a cutting plane 2108P (FIGS. 43 and 44) that can be flush to the cutting surface 2108 can also extend perpendicular to the planar surface 2106.

A central holder 2110 can be integrally formed with or otherwise secured to the planar surface 1906. The central holder 2110 can be a hollow structure with a proximal-facing surface 2110p, a distal-facing surface 2110d, and a lumen 2110L extending therebetween. The proximal-facing surface 2110p can face away from the cutting plane 2108P and the distal-facing surface 2110d can face towards and can be flush with the cutting plane. The lumen 2110L can extend through the proximal and distal facing surfaces 2110p, 2110d of the central holder 2110 and can be sized to receive the access port 2102 therethrough. A longitudinal axis A of the lumen 2110L can extend perpendicular to the cutting plane 2108P (FIG. 42).

In some embodiments, an access port guide 2111 can extend proximally from the central holder 2110 along the longitudinal axis A of the lumen 2110L. The guide 2111 can include a tubular body 2113 that can receive the access port 2102 when the access port is placed into the central holder 2110. A knob 2115 can be rotated such that a length of the tubular body 2113 extending proximally from the central holder 2110 can be adjusted. A support 2117 can extend proximally from the planar surface 2106 of the base 2104 and can hold at least one of the access port 2102, the knob 2115, or the tubular body 2113 such that longitudinal axes of the access port, the tubular guide 2111, and the central holder 2110 can be co-linear. In some embodiments, at least a portion of the tubular body 2113 can include an outer thread 2119 that can engage with which a counterpart internal thread (not shown) of the central holder 2110 and can facilitate adjustment of the guide 2111 relative thereto. The outer surface of the tubular body 2113 can include one or more visual markers 2121 that can indicate to a user a distance from a particular point on the tubular body to the distal-facing surface 2110d of the central holder, i.e., to the cutting plane 2108P. Accordingly, the access port guide 2111 can be used to assist in placing and adjusting the access port 2102 within the central holder 2110 such that a desired length of the access port can extend proximally from the cutting plane 2108P.

The access port cutter 2100 can also include one or more angled holders, such as a first angled holder 2112a, a second angled holder 2112b, a third angled holder 2112c, and a fourth angled holder 2112d. Each angled holder 2112a, 2112b, 2112c, 2112d can be integrally formed with or otherwise secured to the planar surface 2106 of the base 2104. In some embodiments, each angled holder 2112a, 2112b, 2112c, 2112d can have a generally planar component 2114a, 2114b, 2114c, 2114d with a proximal-facing side 2116a, 2116b, 2116c, 2116d that can face away from the cutting plane 2108P, a distal-facing side 2118a, 2118b, 2118c, 2118d that can face towards the cutting plane, and an opening (not shown) extending from the first side through the second side. The planar component 2114a, 2114b, 2114c, 2114d of the angled holder 2112a, 2112b, 2112c, 2112d can extend normal to the planar surface 2106 and can be placed such that a central longitudinal axis AA, AB, AC, AD of the opening of the angled holder can extend at an oblique angle $\alpha 1$, $\alpha 2$, $\alpha 3$, $\alpha 4$ relative to the cutting plane 2108P. In some embodiments, each of the angled holders 2112a, 2112b, 2112c, 2112d can be placed such that each angled holder can extend at a different oblique angle $\alpha 1$, $\alpha 2$, $\alpha 3$, $\alpha 4$ relative to cutting plane 1908P. For example, the first angled holder 2112a can extend at the angle $\alpha 1$, which can be less than the angle $\alpha 2$ of the second angled holder 2112b. Further, in some embodiments, the third angled holder 2112c can extend at the angle $\alpha 3$ which can mirror the angle $\alpha 2$ of the second angled holder 2112b, and the fourth angled holder 2112d can extend at the angle $\alpha 4$ that can mirror the angle $\alpha 1$ of the first angled holder 2112a. A tubular extension 2120a, 2120b, 2120c, 2120d can circumscribe the opening of the planar component 2114a, 2114b, 2114c, 2114d and can extend distally therefrom to the cutting plane 2108P such that a distal-surface of the tubular extension can be flush with the cutting plane. The opening of the planar component 2114a, 2114b, 2114c, 2114d and the tubular extension 2120a, 2120b, 2120c, 2120d can each be sized and shaped to receive the access port 2102 therein.

Figure 43:
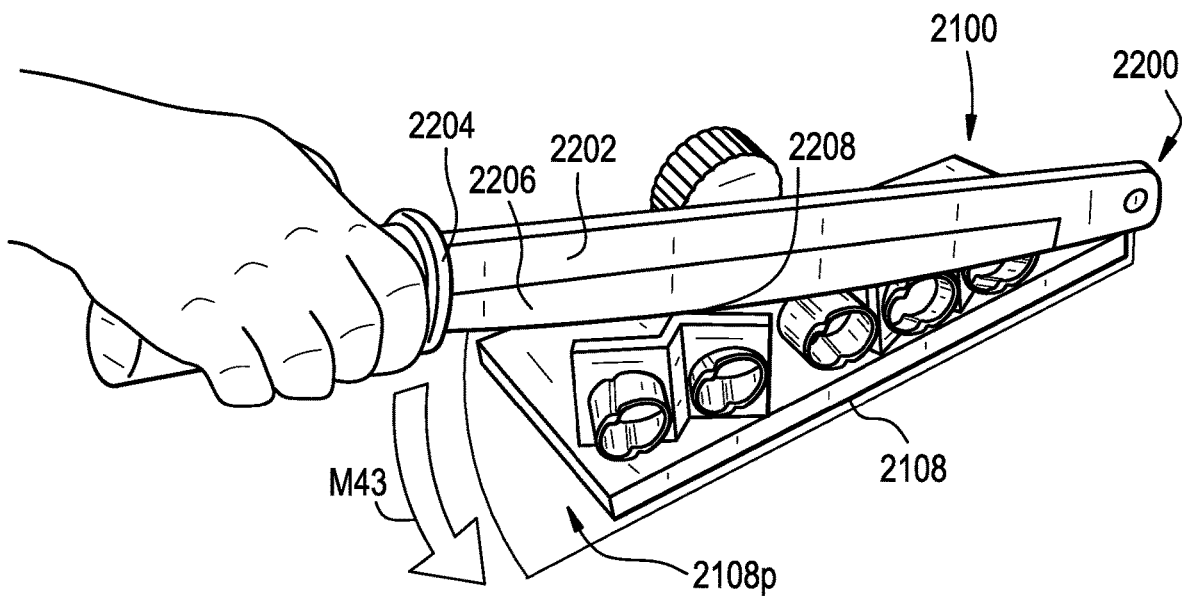
FIG. 43 is a perspective view of the access port cutter of FIG. 41A with one embodiment of a cutting mechanism.

FIG. 43 shows a perspective view of the access port cutter 2100 with a guillotine-style cutting assembly 2200. The cutting assembly 2200 can include a handle 2202 with a grip 2204. The handle 2202 can have a blade 2206 with a cutting edge 2208. The handle 2202 can be attached to the base 2104 of the access port cutter 2100 such that the handle can pivot relative to the base and the blade 2206 can move along the cutting plane 2108P to the cutting surface 2108. The blade 2206 can extend along a length of a lower portion of the handle 2202 such that the cutting edge 2208 can move along the cutting plane 2108P flush across each of the distal-facing surfaces of the angled holders 2112a, 2112b, 2112c, 2112d and the central holder 2110. More particularly, a user can move the grip 2204 from an initial position in which the handle 2202, the blade 2206, and the cutting edge 2208 are located above i.e., remote to, the cutting surface 2108 with a motion M43 towards the cutting surface such that the handle, blade, and cutting edge move along the cutting plane 2108P towards the cutting surface. The handle 2202 can be moved such that the cutting edge 2208 of the blade 2206 can cut across the access port 2102 that can be received within any one of the central holder 2110 or the angled holders 2112a, 2112b, 2112c, 2112d.

Figure 44:
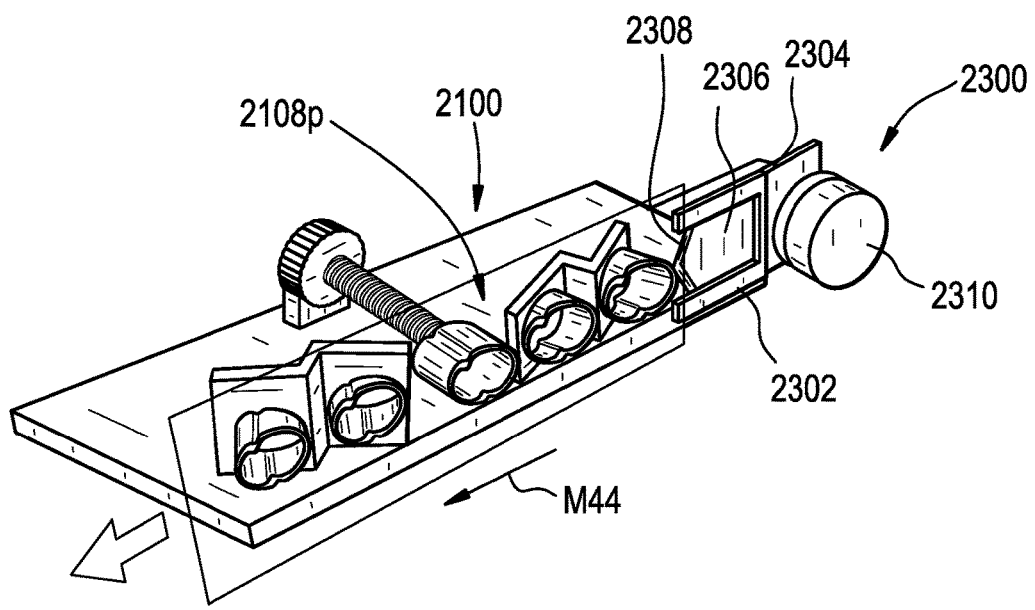
FIG. 44 is a perspective view of the access port cutter of FIG. 41A with another embodiment of a cutting mechanism.

FIG. 44 shows a perspective view of the access port cutter 2100 with a slide cutting assembly 2300. The slide cutting assembly 2300 can have a shuttle 2302 that can receive a blade cartridge 2304 with a blade 2306 therein. In some embodiments, the blade cartridge 2304 and blade 2306 can be similar or identical to the cartridge 200 and blade 112 described above. The shuttle 2302 can be slidably attached to the access port cutter 2100 such that a cutting edge 2308 of the blade 2306 can translate along the cutting plane 2108P flush to each of the distal-facing surfaces of the angled holders 2112a, 2112b, 2112c, 2112d and the central holder 2110. A grip 2308 can extend from the shuttle 2302 and can be used to drive the shuttle 2302 along the cutting plane 2108P. For example, a user can grasp and move the grip 2308 in a cutting direction M44 to drive the shuttle 2302 and, accordingly, the blade 2302 along the cutting plane 2108P across the distal-facing surfaces of one or more of the angled holders 2112a, 2112b, 2112c, 2112d and the central holder 2110 and can cut across the access port 2102 received within one of the angled holders and the central holder.

In use, the access port 2102 can be inserted into any one of the central holder 2110 or angled holders 2112a, 2112b, 2112c, 2112d until a desired length of the access port can extend proximally along the longitudinal axis from the distal-facing surface of the respective central or angled holder. In some embodiments, the central holder 2110 can be used to cut the access port 2102 to the desired length with a straight cut. The access port 2102 can then be inserted into one of the angled holders 2112a, 2112b, 2112c, 2112d such that the distal end of the access port 2102 can be cut with a bevel of a desired angle. In other embodiments, the access port 2102 can be initially placed into the angled holder 2112a, 2112b, 2112c, 2112d. The cutting assembly 2200, 2300 can then be operated as described above such that the cutting edge 2208, 2308 of the blade 2206, 2306 can traverse the cutting plane 2108P flush with the distal-facing surface of each of the central holder and the angled holders. Accordingly, the access port 2102 can be cut to the desired length with the single motion M43, M44 of the blade 2206, 2306 regardless of which holder the access port is received within.

The instruments disclosed herein can be constructed from any of a variety of known materials. Such materials include those which are suitable for use in surgical applications, including metals such as stainless steel, titanium, nickel, cobalt-chromium, or alloys and combinations thereof, polymers such as PEEK, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material, such as carbon fiber and/or high-strength polymers, so as not to interfere with visualization of other structures.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although specific embodiments are described above, changes may be made within the spirit and scope of the concepts described. For example, while the devices and methods disclosed herein are generally described as operable by hand, in some embodiments, access port cutters disclosed herein can be operated, for example, by a robot, motor, a hydraulic driver, etc. Accordingly, it is intended that this disclosure not be limited to the described embodiments, but that it have the full scope defined by the language of the claims. All publications and references cited herein are expressly incorporated herein by reference in their entirety.

The invention claimed is:

1. A surgical instrument, comprising:
a base with an opening configured to receive a surgical access port therein;
a blade configured to translate linearly along at least a portion of the base in a first plane; and
a handle pivotably coupled to the base;
wherein the handle is configured to pivot relative to the base about an axis parallel to the first plane to linearly translate the blade in the first plane along at least a portion of the base such that the blade traverses the opening to cut through a surgical access port received within the opening.

2. The instrument of claim 1, wherein the handle includes a first engagement feature and the blade includes a second engagement feature, wherein the first engagement feature is configured to engage with the second engagement feature to linearly translate the blade along the at least a portion of the base.

3. The instrument of claim 2, wherein the first engagement feature is a pinion gear and the second engagement feature is a gear rack.

4. The instrument of claim 1, wherein the blade is part of a blade cartridge slidably received within the base portion, and
wherein the blade cartridge includes a retention feature configured to hold the blade away from the opening.

5. The instrument of claim 1, further comprising a lock feature to prevent operation of the handle.

6. The instrument of claim 5, wherein the lock feature is a bi-directional lockout pin extending through the handle.

7. The instrument of claim 1, further comprising an extension circumscribing the opening and extending proximally therefrom.

8. The instrument of claim 7, wherein the extension includes at least one interference feature configured to engage waste material of an access port body received within the opening.

9. The instrument of claim 1, wherein a longitudinal axis of the opening extends at an oblique angle relative to the portion of the base along which the blade translates such that the blade traverses the opening to cut through the surgical access port at an oblique angle.

10. An surgical system, comprising:
an access port cutter having a base with at least one opening configured to receive an access port therein, a blade, and a handle; and
an access port having a proximal end, a distal end, and a lumen extending therebetween,
wherein the handle is configured to pivot about an axis to linearly translate the blade in a plane to cut across the access port received within the opening;
wherein the pivot axis is parallel to the blade translation plane.

11. The system of claim 10, wherein the access port cutter opening includes a feature that exerts a force on the access port.

12. The system of claim 10, wherein the access port has a non-circular shape.

13. The system of claim 10, wherein the blade is configured to cut across the access port at an oblique angle relative to a central longitudinal axis of the access port.

14. A surgical method, comprising:
   inserting an access port body into an opening of an access port cutter, the access port cutter having a base portion with the opening, a blade, and a handle;
   pivoting the handle about an axis that is parallel to a plane of the blade to linearly drive the blade along at least a portion of the base; and
   cutting the access port body by passing the blade linearly across the opening of the access port cutter.

15. The method of claim 14, further comprising inserting a distal end of the access port into a patient before cutting the access port body.

16. The method of claim 14, wherein cutting the access port body occurs without deforming a perimeter shape of the access port body.

17. The method of claim 14, wherein inserting the access port body into the opening of the access port cutter further comprises inserting the access port body such that a desired length of the access port body extends distally from the opening.

* * * * *